US011116067B2

(12) United States Patent
Hobro et al.

(10) Patent No.: US 11,116,067 B2
(45) Date of Patent: Sep. 7, 2021

(54) RENAL FAILURE THERAPY SYSTEM HAVING ELECTRICALLY FLOATING FLUID PATHWAY

(71) Applicant: GAMBRO LUNDIA AB, Lund (SE)

(72) Inventors: Sture Hobro, Lund (SE); Erik Torgny, Lund (SE); Par Lofgren, Lund (SE)

(73) Assignee: Gambro Lundia AB, Lund (SE)

( * ) Notice: Subject to any disclaimer, the term of this patent is extended or adjusted under 35 U.S.C. 154(b) by 751 days.

(21) Appl. No.: 15/766,087

(22) PCT Filed: Oct. 14, 2016

(86) PCT No.: PCT/EP2016/074706
§ 371 (c)(1),
(2) Date: Apr. 5, 2018

(87) PCT Pub. No.: WO2017/064248
PCT Pub. Date: Apr. 20, 2017

(65) Prior Publication Data
US 2018/0310391 A1    Oct. 25, 2018

(30) Foreign Application Priority Data

Oct. 14, 2015  (SE) .................................... 1551324-5

(51) Int. Cl.
*H05F 3/02* (2006.01)
*A61M 1/34* (2006.01)
(Continued)

(52) U.S. Cl.
CPC ................. *H05F 3/02* (2013.01); *A61M 1/16* (2013.01); *A61M 1/1621* (2014.02); *A61M 1/34* (2013.01);
(Continued)

(58) Field of Classification Search
CPC ...... A61M 1/14–3496; A61M 5/16831; A61M 2205/3317; A61M 2205/70–702; H05F 3/00–02; H05F 1/00–02
See application file for complete search history.

(56) References Cited

U.S. PATENT DOCUMENTS 4,059,847 A   11/1977 Phillips et al.
4,155,852 A   5/1979  Fischel et al.
(Continued)

FOREIGN PATENT DOCUMENTS

DE   3512533   10/1986
EP   0458041   11/1991
(Continued)

OTHER PUBLICATIONS

Notice of Opposition filed by Fresenius Medical Care AC & Co KGaA in related EP Patent Application No. 2616117B1 on Sep. 9, 2016.
(Continued)

*Primary Examiner* — Jared Fureman
*Assistant Examiner* — Christopher J Clark
(74) *Attorney, Agent, or Firm* — K&L Gates LLP

(57) ABSTRACT

A renal failure therapy system (10) includes a dialyzer (102); a blood circuit (100) in fluid communication with the dialyzer (102); a dialysis fluid circuit (30) in fluid communication with the dialyzer (102); and an electrically floating fluid pathway (140) comprising at least a portion of the blood circuit (100) and at least a portion of the dialysis fluid circuit (30), wherein the only electrical path to ground is via used dialysis fluid traveling through machine (12) to earth ground (28), and wherein at least one electrical component (46, 90, 82, 66, 102, 116) in the at least a portion of the dialysis fluid circuit (30) of the electrically floating fluid pathway (140) is electrically bypassed.

26 Claims, 14 Drawing Sheets

(51) Int. Cl.
*A61M 1/36* (2006.01)
*A61M 1/16* (2006.01)

(52) U.S. Cl.
CPC .......... *A61M 1/3413* (2013.01); *A61M 1/367* (2013.01); *A61M 1/3621* (2013.01); *A61M 2205/18* (2013.01); *A61M 2205/3317* (2013.01); *A61M 2205/3331* (2013.01); *A61M 2205/3334* (2013.01); *A61M 2205/3344* (2013.01); *A61M 2205/3351* (2013.01); *A61M 2205/3368* (2013.01); *A61M 2205/502* (2013.01); *A61M 2205/581* (2013.01); *A61M 2205/583* (2013.01); *A61M 2205/70* (2013.01); *A61M 2205/702* (2013.01)

(56) References Cited

U.S. PATENT DOCUMENTS

| | | | |
|---|---|---|---|
| 4,443,333 | A | 4/1984 | Mahurkar |
| 5,578,223 | A | 11/1996 | Bene et al. |
| 5,657,000 | A | 8/1997 | Ellingboe |
| 5,736,038 | A | 4/1998 | Stoughton |
| 6,136,201 | A | 10/2000 | Shah et al. |
| 8,180,443 | B1 | 5/2012 | Kleinekofort et al. |
| 10,569,007 | B2 * | 2/2020 | Hobro ................. A61M 1/3413 |
| 2003/0195453 | A1 * | 10/2003 | Han .................... A61M 1/3661 604/5.01 |
| 2003/0209475 | A1 | 11/2003 | Connell et al. |
| 2003/0218623 | A1 | 11/2003 | Krensky et al. |
| 2003/0220598 | A1 | 11/2003 | Busby et al. |
| 2004/0019312 | A1 | 1/2004 | Childers et al. |
| 2004/0267183 | A1 | 12/2004 | Chevallet |
| 2005/0045540 | A1 | 3/2005 | Connell et al. |
| 2005/0131332 | A1 | 6/2005 | Kelly et al. |
| 2006/0177351 | A1 | 8/2006 | Heiniger et al. |
| 2008/0065006 | A1 | 3/2008 | Roger et al. |
| 2008/0200866 | A1 | 8/2008 | Prisco et al. |
| 2009/0177149 | A1 | 7/2009 | Childers et al. |
| 2010/0022935 | A1 | 1/2010 | Muller |
| 2010/0312161 | A1 | 12/2010 | Jonsson et al. |
| 2011/0185722 | A1 | 8/2011 | Sebesta et al. |
| 2013/0158469 | A1 | 6/2013 | Hopping et al. |
| 2013/0165848 | A1 | 6/2013 | Sebesta et al. |
| 2013/0319920 | A1 * | 12/2013 | Hansson .............. A61M 1/3621 210/143 |
| 2013/0324900 | A1 | 12/2013 | Wariar et al. |

FOREIGN PATENT DOCUMENTS

| | | |
|---|---|---|
| EP | 0611228 | 8/1994 |
| EP | 0820776 | 1/1998 |
| FR | 2547504 | 12/1984 |
| GB | 927349 | 5/1963 |
| JP | 1024102 | 1/1998 |
| JP | 1085323 | 4/1998 |
| WO | 9306875 | 4/1993 |
| WO | 9411093 | 5/1994 |
| WO | 2005044339 | 5/2005 |
| WO | 2008031539 | 3/2008 |
| WO | 2009044220 | 4/2009 |
| WO | 2010011441 | 1/2010 |
| WO | 2010077762 | 7/2010 |

OTHER PUBLICATIONS

Eidesstattliche Versicherung von Herrn Dr. Jorg Dreyhsig. Affidavit of Dr. Jorg Dreyhsig asserting the booklet referred to as D13 (Fresenius Medical Care: Prospekt: Acute Therapy Systems: multiFiltrate, 2006) was available to the public at the ERA-EDTA conference in Glasgow, UK in 2006. D13.
DIN EN 60601-1 (VDE 0750-1), Seiten 84-87 (Jul. 2007). Medical electrical equipment—Part 1 : General requirements for basic safety and essential performance (IEC 60601-1 :2005); German version EN 60601-1:2006. D16.
C. Ronco et al., "Critical Care Nephrology," Kluwer Academic Publishers, 1998. 7 pages. D12.
Ansiiaami ES1-1993. American National Standard. Current safe limits for electromedical apparatus. Developed by Association for the Advancement of Medical Instrumentation. Dec. 2, 1993. D15.
Jonsson et al., "Blood lines conduct leakage current during haemodialysis: a potential safety risk during first failure, especially for patients with central dialysis catheter as access", Med. Bioi. Eng. Comput., 2005, 43, 731-738, 8 total pages.
Non-Final Office Action issued in U.S. Appl. No. 13/824,892 dated Jul. 14, 2016.
Final Office Action issued in U.S. Appl. No. 13/824,892 dated Jan. 25, 2017.
Non-Final Office Action issued in U.S. Appl. No. 13/824,892 dated Jul. 11, 2017.
Response to the Non-Final Office Action dated Jul. 11, 2017 in U.S. Appl. No. 13/824,892. Response dated Nov. 8, 2017.
Final Office Action issued in U.S. Appl. No. 13/824,892 dated Feb. 22, 2018.
International-Type Search Report issued in related Swedish Patent Application No. SE1551324-5 dated May 4, 2016.
Office Action issued in related Swedish Patent Application No. SE1551324-5 dated May 4, 2016.
International Search Report issued in International Patent Application No. PCT/EP2016/074706 dated Jan. 3, 2017.
Written Opinion issued in International Patent Application No. PCT/EP2016/074706 dated Jan. 3, 2017.

* cited by examiner

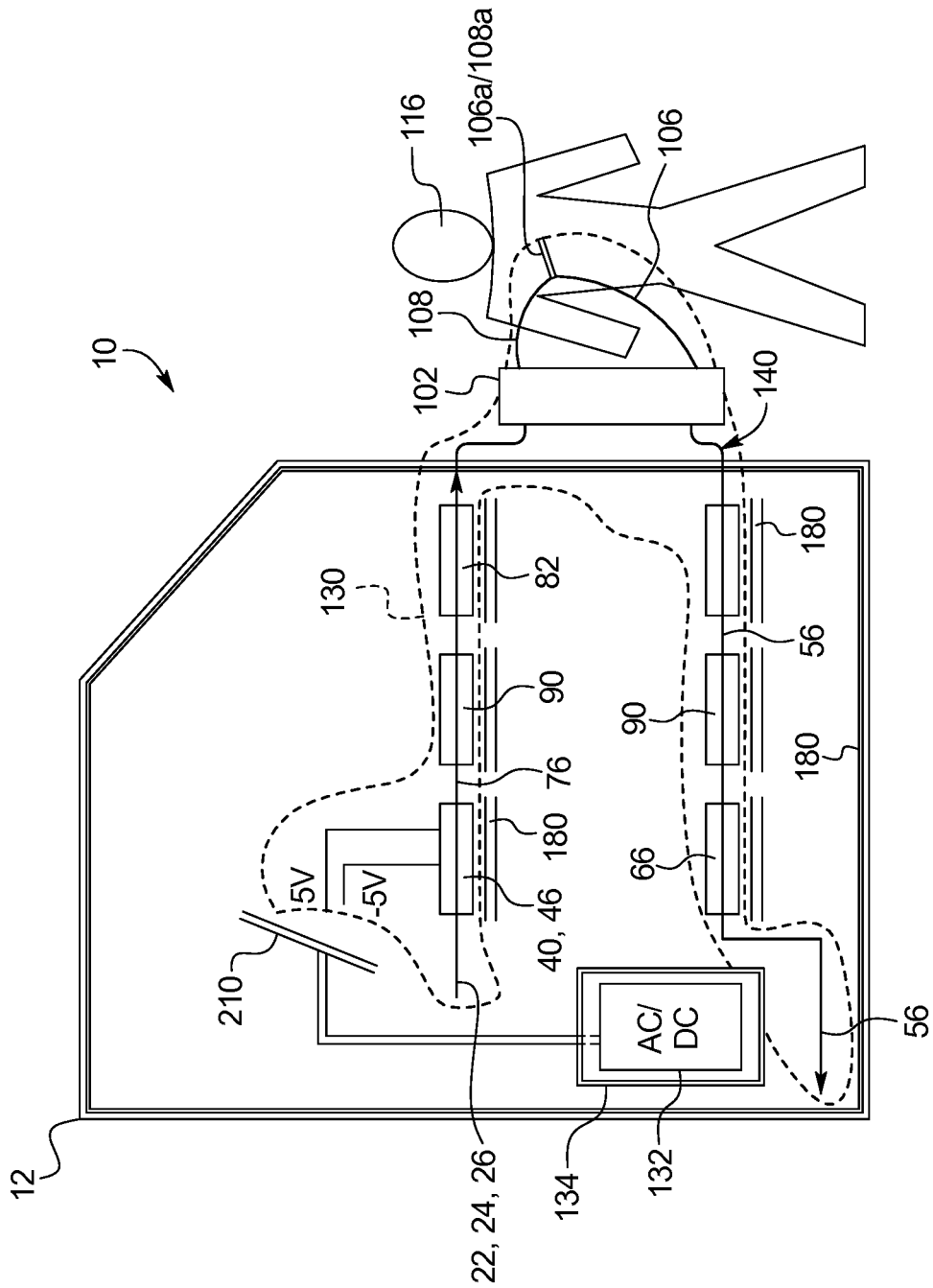

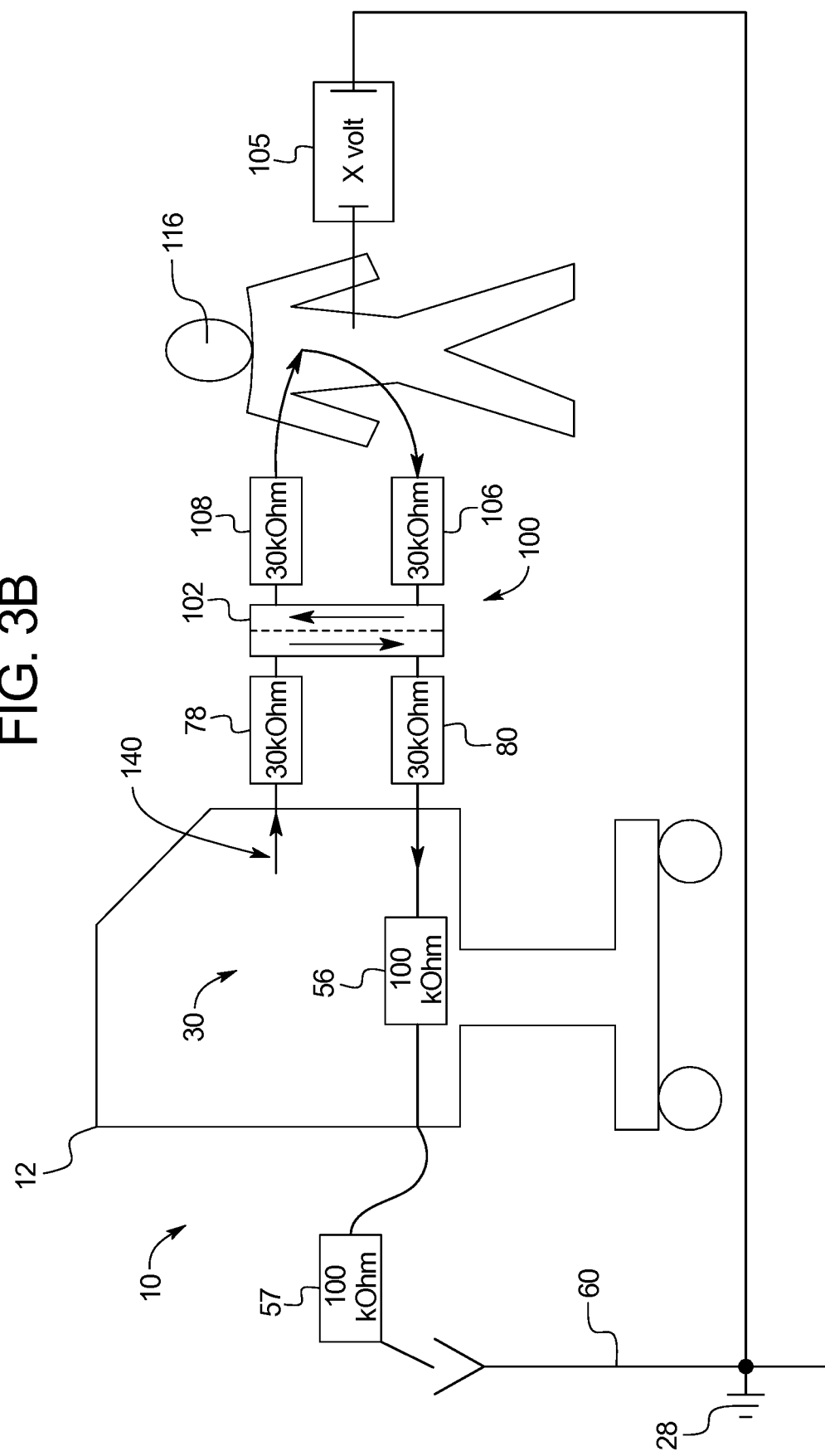

RENAL FAILURE THERAPY SYSTEM HAVING ELECTRICALLY FLOATING FLUID PATHWAY

PRIORITY CLAIM

The present application is a National Phase of International Application No. PCT/EP2016/074706, filed on Oct. 14, 2016, which claims priority to Swedish Patent Application No. 1551324-5, filed on Oct. 14, 2015, the entire contents of each of which are being incorporated herein by reference.

BACKGROUND

The present disclosure relates generally to medical systems. More specifically, the present disclosure relates to electrical isolation for medical fluid systems, such as the renal failure therapy systems.

Hemodialysis ("HD") in general uses diffusion to remove waste products from a patient's blood. A diffusive gradient that occurs across the semi-permeable dialyzer between the blood and an electrolyte solution called dialysis fluid causes diffusion. Hemofiltration ("HF") is an alternative renal replacement therapy that relies on a convective transport of toxins from the patient's blood. This therapy is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism, which is particularly beneficial in removing middle and large molecules (in hemodialysis there is a small amount of waste removed along with the fluid gained between dialysis sessions, however, the solute drag from the removal of that ultrafiltrate is typically not enough to provide convective clearance).

Hemodiafiltration ("HDF") is a treatment modality that combines convective and diffusive clearances. HDF flows dialysis fluid through a dialyzer, similar to standard hemodialysis, providing diffusive clearance. In addition, substitution solution is provided directly to the extracorporeal circuit, providing convective clearance. These modalities are administered by a dialysis machine. The machines may be provided in a center or in a patient's home. Dialysis machines provided in a center are used multiple times a day for multiple patients and therefore must be cleaned between treatments. Dialysis machines use multiple components, including electrical components.

Outside electrical devices have the potential to expose people to the risk of spurious electric currents. In the case of medical electrical equipment (and dialysis machines in particular), the risk is potentially greater since patients connected to such equipment may be exposed to larger risk due to how the equipment is connected to the patient and not benefit from the protection factors that apply to people not so connected. Patients connected to present dialysis machines may be poorly safeguarded against leakage current due to contact with external electrical equipment, such as bed lamps, electrically adjustable beds or treatment chairs, lab tops and phones connected to chargers other electrical equipment that is in turn connected to an electrical power source.

It is accordingly desirable to make medical devices, such as renal failure therapy machines, including HD, HF and HDF machines electrically safer for the patient.

SUMMARY

The present disclosure provides a renal failure therapy system and method that performs hemodialysis ("HD"), hemofiltration ("HF") and hemodiafiltration ("HDF"). Accordingly, "renal failure therapy" as used herein is meant to include any one, or more, or all of HD, HF and/or HDF.

The renal failure therapy system of the present disclosure maintains a floating fluid pathway that extends to and through the patient via arterial and venous blood lines. In one embodiment, floating fluid pathway means a fluid pathway which, when carrying an electrically conductive fluid therein, would itself render the conductive fluid electrically floating relative to an electrical potential, such as ground, provided to the dialysis machine through the mains and/or through grounded parts connected to the dialysis machine (e.g. drain and external water lines). The floating fluid pathway may include the entire or one or several portion(s) of the blood lines (including the needles and catheter), (fresh and/or used) dialysis fluid lines, concentrate lines, and/or water lines as well as components, such as sensors and pumps, connected to the above mention fluid lines.

Machines currently on the market are typically grounded at multiple locations within the machine. The floating fluid pathway of the present on the other hand is not connected to ground. The floating fluid pathway extends to an external drain line, which runs to earth ground. The impedance between the patient through the floating fluid pathway and the external drain line (where a protective earth system may be anticipated) is accordingly relatively high compared to known systems. The floating fluid pathway is therefore safer against faulty external electrical equipment than machines currently on the market. Also, the resistance of the floating fluid pathway which may be in combination with the resistance of an external drain line is high enough that the voltage needed to reach a maximum allowable current through the patient, e.g., fifty microamperes (50 µA) for central venous catheters, is also relatively high compared to machines currently on the market. The voltage needed will be higher than a faulty voltage created inadvertently, e.g., via static electricity, electromagnetic radiation ("EMR") or via a leakage current from any mains connected device compared to machines currently on the market.

The floating fluid pathway flows through fluids used in the renal failure therapy system. One fluid is the patient's blood, which is pumped through the arterial and venous blood lines and needles (or catheter). Another fluid is dialysis fluid produced and pumped through the fresh and used sides of a dialysis fluid circuit (including concentrate used to prepare the dialysis fluid). A further fluid is replacement or substitution fluid, which is typically refined from the dialysis fluid and pumped directly to the arterial or venous line. Certain hardware components, such as sensors, may be adversely effected by current flowing through the dialysis fluid and blood. For example, conductivity sensors typically have probes that extend into the fluid to measure the conductivity of same. Current flowing through the fluid due to an electrical fault may interrupt and/or corrupt the operation and/or readout of the conductivity sensor. The same is true for flowmeters that measure electrical or magnetic properties, where current flow due to faulty conditions may interrupt and/or corrupt the operation of and/or readout from the flowmeter.

The floating fluid pathway of the present disclosure dissipates stray currents or induced currents in the fluid pathways caused, e.g., by an electromagnetic field from other apparatuses located close to the dialysis machine. For example, microwave ovens located in nearby rooms, electrical trains (e.g., thirty or fifty meters from the machines), elevators, drilling machines, high voltage electrical, e.g., radiology or x-ray machines, etc.), thunderstorms or even geomagnetic flows inside the earth or induced from storms at the sun may cause such stray currents.

Certain components in the fluid pathways will have a conductive portion that electrically contacts the dialysis fluid or blood and an insulated, e.g., mounting portion. The conductive portion becomes part of the overall applied part. In general, the applied part for purposes of this application is the extracorporeal circuit and any component or "part" that is conductively connected to the extracorporeal circuit, which accordingly brings in the dialysis fluid (including concentrates and potentially purified water) via the dialyzer, any substitution fluid directly contacting the blood, and any additional conductive component or "part" that contacts the blood, dialysis fluid or substitution fluid. The insulated portion of the component serves to create a portion of a well defined applied part. For example, a dialysis fluid pump, such as a gear pump, may have a conductive body that shares current flow with dialysis fluid flowing through the conductive body in a proportion depending on the relative resistances of the dialysis fluid path and the conductive component. In the system of the present disclosure, the insulating portion electrically insulates the conductive pump housing, and the dialysis fluid flowing through it, from the rest of the machine.

Components in the fluid pathways adding to the overall applied part are electrically insulated from the machine chassis or frame. For example, if the component is mounted to the machine chassis, an insulating barrier or pad will be placed between the component and the chassis. The insulating pad will isolate the component itself, as well as conductive hardware for mounting the component, from the chassis or frame. In this manner, a fault in a component, like a conductivity cell that is part of the applied part will not result in a current that may harm the patient.

The components adding conductive portions to the overall applied part may additionally have electrical signal lines leading to and from the conductive portions. Those electrical signal lines therefore also need to be electrically isolated from the rest of the machine because they may likewise carry leakage currents. Discussed in detail below is structure and methodology for electrically isolating the electrical signal lines.

The present disclosure includes structure and methodology to allow the floating fluid pathway to operate with sensitive electrical equipment. Bypass lines are provided for the sensitive equipment in one embodiment. Here, an electrode, conductor or wire of very little resistance is provided to entice the current flowing in the dialysis fluid or blood into a bypass line and away from the sensitive equipment. Current is reintroduced into the dialysis fluid or blood downstream of the sensitive equipment, such that the equipment is bypassed and left to operate properly.

The bypass line may include conductive couplers placed in the fluid lines upstream and downstream, respectively, of the electrically sensitive components or equipment. Electrically sensitive components or equipment may be those that are sensitive to electrical disturbances, such as measuring components like conductivity sensors and electrical flow meters. The conductive couplers may be carbon couplers, metallic couplers or conductive polymer couplers, such as polymers containing carbon or other conductive filler. An electrical line, wire or conductor is extended from the upstream conductive coupler to the downstream conductive coupler. The electrical line, wire or conductor may be placed in an electrically insulating tube, casing, coating, etc. A bypass line may be provided for each electrically sensitive component. In one embodiment, multiple bypass lines may be provided in both the fresh and used dialysis fluid lines, and the blood lines if needed.

It is also contemplated to bypass the dialyzer and the patient by placing a wire or conductor, e.g., a short circuit, between the fresh and used dialysis fluid lines and close to the connection between the dialysis fluid lines and the dialyzer. This shortcut electrical line bypass shunts current due to a fault that develops in the dialysis fluid circuit and prohibits the fault current from reaching sensitive electrical equipment, such as sensing equipment. The bypass line may alternatively be formed via a fluid bypass line, e.g., a dialysis fluid line extending between the fresh and used dialysis fluid lines. Electrical resistance in the conductive dialysis fluid is relatively high (e.g. a few kOhms over a twenty to thirty centimeter run for example compared to less than a hundredth of an Ohm for the same distance of a copper wire), so that the dialysis fluid bypass line is relatively short in one embodiment. Further, a bypass valve located in the dialysis fluid bypass line between fresh and used dialysis fluid that closes flow in the line (normally closed during treatment) may have a portion that is part of the overall applied part, which is accordingly conductive enough also in its closed orientation (so there is no fluid flow) to shortcut any current/voltage away from the fresh and used dialysis fluid lines. The dialyzer itself also acts as an electrical bypass of the patient between the fresh and used dialysis fluid lines.

The floating fluid pathway of the renal failure therapy system of the present disclosure operates in one embodiment with a structure for testing whether the floating fluid pathway is operating properly. The structure may include an electrical path from the electrical bypass system to earth ground and a current meter located in the electrical path. A large resistor may be placed in the electrical path so that any resulting current is not too large. If the current meter senses too large a current, then a controller or logic implementer of the system determines that the floating fluid pathway has somehow been compromised and sounds and/or displays an audio, visual or audiovisual alarm. The nurse may then halt the beginning of a treatment before the patient is connected to the machine, e.g., during priming.

In another testing embodiment, a current or voltage generator and a voltage or current meter are placed in electrical communication with fresh or spent dialysis fluid (flow path resistance) somewhere in the dialysis fluid circuit. The current or voltage generator is also placed in electrical series with a switch. When the switch is closed, current or voltage is generated in or across the flow path resistance. This is done prior to treatment or patient connection to the machine. For example, a generated current may be set at a limit for operation with a central venous catheter in one embodiment. A voltage meter then reads the corresponding voltage, which is stored in a memory. During treatment, the switch is opened, so that current or voltage is no longer generated in the flow path resistance. However, the voltage or current meter may still look for stray or fault voltages or currents during treatment. If for example a voltage meter during treatment reads a voltage at or above the voltage stored from the test period when the limit current was applied, the machine places itself in a safe mode, shuts down treatment and provides an audio, visual or audiovisual alarm. If the measured voltage during treatment remains below the voltage stored from the test period when the limit current was applied, treatment is allowed to continue.

In a further testing embodiment, a current or voltage generator and a voltage or current meter as just described are placed in electrical communication with two of the electrical bypasses instead of direct communication with fresh or spent dialysis fluid. The two bypasses may be any of the bypasses described herein, and in one embodiment are bypasses located closer to the dialyzer.

In light of the technical features set forth herein, and without limitation, in a first aspect, a renal failure therapy system includes: a dialyzer; a blood circuit in fluid communication with the dialyzer; a dialysis fluid circuit in fluid communication with the dialyzer; and an electrically floating fluid pathway comprising at least a portion of the blood circuit and at least a portion of the dialysis fluid circuit, wherein the only electrical path to ground is via used dialysis fluid traveling through the machine to earth ground, and wherein at least one electrical component sensitive to electrical disturbances in the at least a portion of the dialysis fluid circuit of the electrically floating fluid pathway is electrically bypassed. Electrical components sensitive to electrical disturbances may be components that read out a signal, such as conductivity sensors and electromagnetic flowmeters.

In a second aspect, which may be used with any other aspect described herein unless specified otherwise, at least one of (i) electrically bypassed is electrically short circuited or (ii) the electrical component is of a type sensitive to electrical disturbances.

In a third aspect, which may be used with any other aspect described herein unless specified otherwise, electrically bypassed includes (i) at least one electrical line placed in parallel with the at least one electrically sensitive component, (ii) a small passage (176) formed between a fluid inlet (172) and a fluid outlet (174) to the at least one electrical component (46, 90, 82, 66, 102, 116), or (iii) a conductor (178, 188) located between the fluid inlet (172) and the fluid outlet (174) of the at least one electrical component (46, 90, 82, 66, 102, 116).

In a fourth aspect, which may be used with the third aspect in combination with any other aspect described herein unless specified otherwise, the at least one electrical line placed in parallel with the at least one electrically sensitive component includes upstream and downstream conductive couplers placed in fluid lines upstream and downstream, respectively, of the electrically sensitive component, and wherein the electrical line is extended from the upstream conductive coupler to the downstream conductive coupler.

In a fifth aspect, which may be used with any other aspect described herein unless specified otherwise, the at least one electrically sensitive component includes a conductivity sensor having a conductivity probe that contacts dialysis fluid flowing through the at least a portion of the dialysis fluid circuit.

In a sixth aspect, which may be used with any other aspect described herein unless specified otherwise, the at least one electrically sensitive component includes a flowmeter for measuring the flowrate of dialysis fluid flowing through the at least a portion of the dialysis fluid circuit.

In a seventh aspect, which may be used with any other aspect described herein unless specified otherwise, the at least a portion of the dialysis fluid circuit (30) includes at least a portion of a fresh dialysis fluid line and at least a portion of a used dialysis fluid line.

In an eighth aspect, which may be used with the seventh aspect in combination with any other aspect described herein unless specified otherwise, the system includes at least one electrically bypassed electrically sensitive component in the at least a portion of the fresh dialysis fluid line and at least one electrically bypassed electrically sensitive component in the at least a portion of the used dialysis fluid line.

In a ninth aspect, which may be used with the seventh aspect in combination with any other aspect described herein unless specified otherwise, the electrically floating fluid pathway includes an electrical line extending from the at least a portion of the fresh dialysis fluid line to the at least a portion of the used dialysis fluid line.

In a tenth aspect, which may be used with the ninth aspect in combination with any other aspect described herein unless specified otherwise, the electrical line is positioned to bypass the dialyzer and the patient.

In an eleventh aspect, which may be used with the seventh aspect in combination with any other aspect described herein unless specified otherwise, the electrically floating fluid pathway includes a bypass line having a valve constructed so as to allow current to flow when closed from the at least a portion of the fresh dialysis fluid line to the at least a portion of the used dialysis fluid line.

In a twelfth aspect, which may be used with any other aspect described herein unless specified otherwise, the electrically floating fluid pathway includes at least one fluid component that is not electrically bypassed, but which is electrically insulated from a chassis of the system to form a delineated applied part.

In a thirteenth aspect, which may be used with any other aspect described herein unless specified otherwise, a renal failure therapy system includes: a dialyzer; a blood circuit in fluid communication with the dialyzer; a dialysis fluid circuit in fluid communication with the dialyzer, the dialysis fluid circuit including a fresh dialysis fluid line and a used dialysis fluid line; a first electrical component sensitive to electrical disturbances operable with the fresh dialysis fluid line; a first electrical bypass shunting current away from the first electrically sensitive component; a second electrical component sensitive to electrical disturbances operable with the used dialysis fluid line; and a second electrical bypass shunting current away from the second electrically sensitive component.

In a fourteenth aspect, which may be used with the thirteenth aspect in combination with any other aspect described herein unless specified otherwise, the first and second electrical bypasses are part of an electrically floating fluid pathway, in which the only electrical path to ground is via used dialysis fluid traveling through the machine to earth ground.

In a fifteenth aspect, which may be used with the fourteenth aspect in combination with any other aspect described herein unless specified otherwise, the electrically floating fluid pathway includes a plurality of fluid operating components located along the fresh dialysis fluid line and the used dialysis fluid line, wherein the fluid operating components are not electrically bypassed.

In a sixteenth aspect, which may be used with the fifteenth aspect in combination with any other aspect described herein unless specified otherwise, the plurality of fluid operating components include at least one of (i) a pump or (ii) a component mounted to a system chassis via an electrical insulator.

In a seventeenth aspect, which may be used with the thirteenth aspect in combination with any other aspect described herein unless specified otherwise, the first and second electrical bypasses contact fluid upstream and downstream of the first and second electrically sensitive components, respectively, wherein the fluid places the first and second bypasses in electrical communication.

In a eighteenth aspect, which may be used with any other aspect described herein unless specified otherwise, a renal failure therapy system includes: a dialyzer; a blood circuit in fluid communication with the dialyzer, the blood circuit including a central venous catheter; a dialysis fluid circuit in fluid communication with the dialyzer; and an electrically floating fluid pathway comprising at least a portion of the blood circuit and at least a portion of the dialysis fluid circuit, wherein the only electrical path to ground is via used dialysis fluid traveling through the machine to earth ground, and wherein the electrically floating fluid pathway ensures electrical safety for operation with the central venous catheter.

In a nineteenth aspect, which may be used with any other aspect described herein unless specified otherwise, a renal failure therapy machine operates with a dialyzer and a blood circuit in fluid communication with the dialyzer, the machine including: a dialysis fluid circuit in fluid communication with the dialyzer, the dialysis fluid circuit including a fresh dialysis fluid line and a used dialysis fluid line; and an electrically floating fluid pathway including an electrical bypass from the fresh dialysis fluid line to the used dialysis fluid line, such that a fault current generated in the fresh dialysis fluid line bypasses the dialyzer via the electrical bypass to the used dialysis fluid line (56).

In a twentieth aspect, which may be used with the nineteenth aspect in combination with any other aspect described herein unless specified otherwise, the electrical bypass is at least one of (i) located between a furthest downstream fluid component of the fresh dialysis fluid line and the dialyzer, or (ii) located between a furthest upstream fluid component of the used dialysis fluid line and the dialyzer.

In a twenty-first aspect, which may be used with the nineteenth aspect in combination with any other aspect described herein unless specified otherwise, the electrical bypass is a first electrical bypass, and which includes at least one additional electrical bypass shunting current away from an electrically sensitive component located in the fresh or used dialysis fluid lines.

In a twenty-second aspect, which may be used with any other aspect described herein unless specified otherwise, a renal failure therapy system includes: a dialyzer; a blood circuit in fluid communication with the dialyzer; a dialysis fluid circuit in fluid communication with the dialyzer; an electrically floating fluid pathway comprising at least a portion of the dialysis fluid circuit, wherein the only electrical path to ground is via used dialysis fluid traveling through the machine to earth ground, and wherein at least one electrical component sensitive to electrical disturbances in the at least a portion of the dialysis fluid circuit of the electrically floating fluid pathway is electrically bypassed; and a structure for testing whether the electrically floating fluid pathway has been compromised via an undesired electrical connection to ground.

In a twenty-third aspect, which may be used with the twenty-second aspect in combination with any other aspect described herein unless specified otherwise, the testing structure includes a current or voltage generator and a voltage meter or current meter, respectively, and wherein the system is programmed to use (i) the generator to set a limit and (ii) the meter to see if the limit has been reached.

In a twenty-fourth aspect, which may be used with the twenty-third aspect in combination with any other aspect described herein unless specified otherwise, the system further includes a switch in electrical communication with the generator, and wherein the system is programmed to close the switch before treatment for (i) and open the switch during treatment for (ii).

In a twenty-fifth aspect, which may be used with the twenty-second aspect in combination with any other aspect described herein unless specified otherwise, the testing structure includes (i) an electrical path from at least one bypass bypassing the at least one electrically sensitive component to ground and (ii) a current meter located in the electrical path.

In a twenty-sixth aspect, which may be used with the twenty-second aspect in combination with any other aspect described herein unless specified otherwise, the testing structure includes a voltage or current meter placed in electrical communication with first and second bypasses, each bypass shunting current away from an electrical component sensitive to electrical disturbances located in the fresh or used dialysis fluid lines.

In a twenty-seventh aspect, which may be used in combination with any other aspect described herein unless specified otherwise, the electrically floating fluid pathway is connected to an external drain line, which leads to an electrically grounded drain.

In a twenty-eighth aspect, which may be used in combination with any other aspect described herein unless specified otherwise, the electrically floating fluid pathway (140) includes arterial line 106, venous line 108, arterial and venous needles 106*a*/108*a*, fresh dialysis fluid line 76, fresh dialysis fluid tube 78, liquid concentrate lines 34 and 36, concentrate sources 24 and 26 if liquid concentrate sources are used, water line 32, water source 22 if the water is non-deionized, used dialysis fluid tube 80, and used dialysis fluid line 56.

In a twenty-ninth aspect, which may be used in combination with any other aspect described herein unless specified otherwise, a renal failure therapy system includes a dialyzer; a blood circuit in fluid communication with the dialyzer; a dialysis fluid circuit in fluid communication with the dialyzer; and an electrically floating fluid pathway comprising at least a portion of the blood circuit and at least a portion of the dialysis fluid circuit, wherein the only electrical path to ground is via used dialysis fluid traveling through the machine to earth ground, and wherein at least one electrical component in the at least a portion of the dialysis fluid circuit of the electrically floating fluid pathway includes an electrical bypass having (i) a small passage (176) formed between a fluid inlet (172) and a fluid outlet (174) to the at least one electrical component (46, 90, 82, 66, 102, 116), or (ii) a conductor located between the fluid inlet and the fluid outlet of the at least one electrical component. The conductor may be a conductive insert between the fluid inlet and the fluid outlet or a wall or partition in a tube, the wall or partition separating the fluid inlet from the fluid outlet.

In a thirtieth aspect, any of the features, functionality and alternatives described in connection with any one or more of FIGS. 1 to 7D may be combined with any of the features, functionality and alternatives described in connection with any of the other one or more of FIGS. 1 to 7D.

It is therefore an advantage of the present disclosure to provide a hemodialysis, hemofiltration or hemodiafiltration system and method having an electrically floating fluid pathway.

It is another advantage of the present disclosure to provide a hemodialysis, hemofiltration or hemodiafiltration system and method having an electrically floating fluid pathway, which is operable with sensitive fluid flow electrical components.

It is a further advantage of the present disclosure to provide a hemodialysis, hemofiltration or hemodiafiltration system and method having an electrically floating fluid pathway, which is relatively inexpensive.

It is yet another advantage of the present disclosure to provide a hemodialysis, hemofiltration or hemodiafiltration system and method having an electrically floating fluid pathway that does not require a large redesign of existing sensors and is thereby easy and cost-effective to implement.

Moreover, it is an advantage of the present disclosure to provide a hemodialysis, hemofiltration or hemodiafiltration system and method having an electrically floating fluid pathway, which may be tested prior to patient connection to ensure that any leakage current in the electrically floating fluid pathway is within an acceptable range.

The advantages discussed herein may be found in one, or some, and perhaps not all of the embodiments disclosed herein. Additional features and advantages of the present invention are described in, and will be apparent from, the following Detailed Description of the Invention and the figures.

BRIEF DESCRIPTION OF THE FIGURES

FIG. 3A is a schematic illustration of one embodiment of a renal failure therapy system including an overall applied part formed via a floating fluid pathway.

FIG. 3B is a schematic illustration of one embodiment of a renal failure therapy system including a floating fluid pathway showing lumped impedances for the blood circuit, the used dialysis fluid portion of the dialysis fluid circuit, and the drain line.

DETAILED DESCRIPTION

Figure 1:
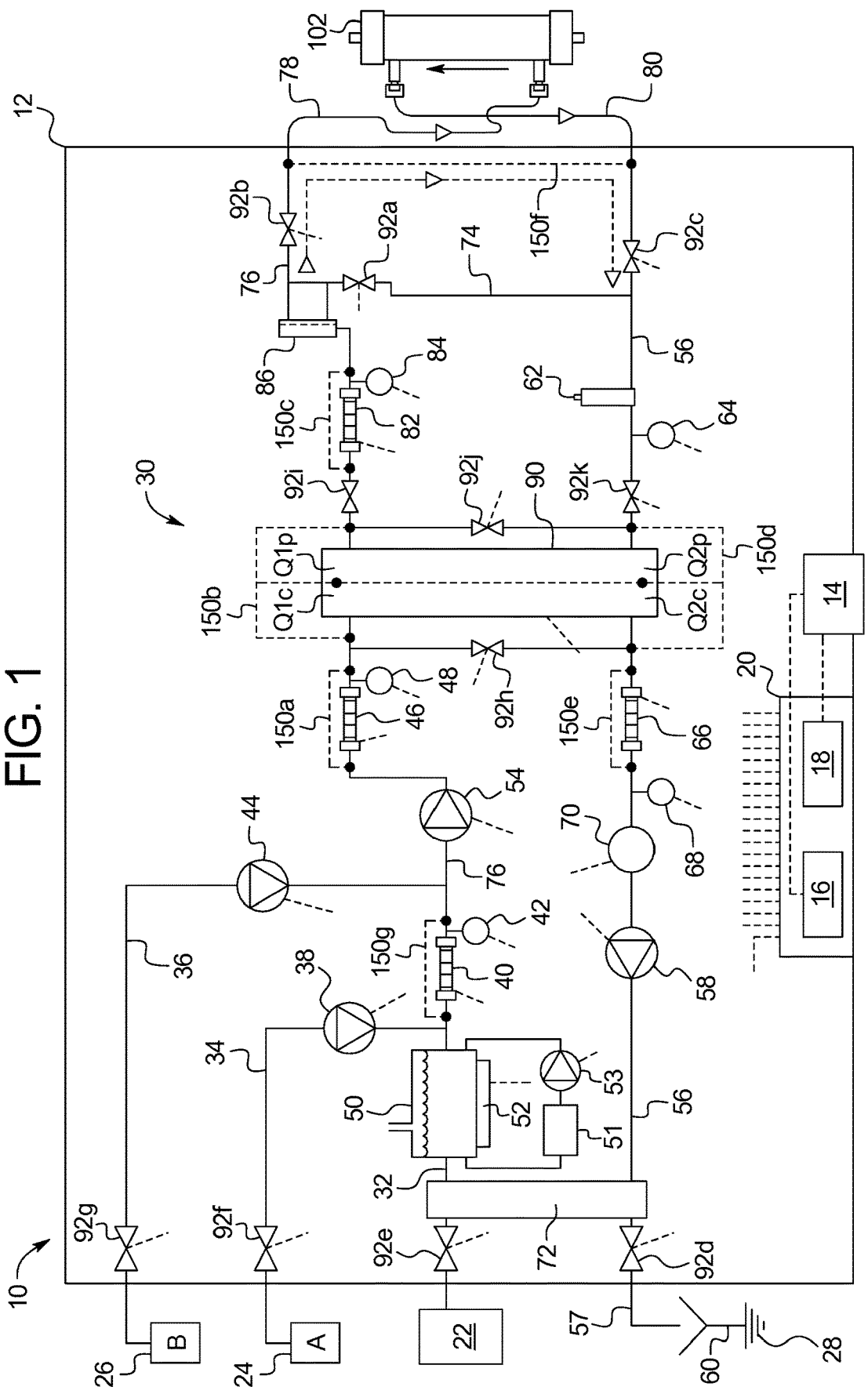
FIG. 1 is a schematic illustration of one embodiment of a dialysis fluid circuit for a renal therapy system having a floating fluid pathway.
Figure 2:
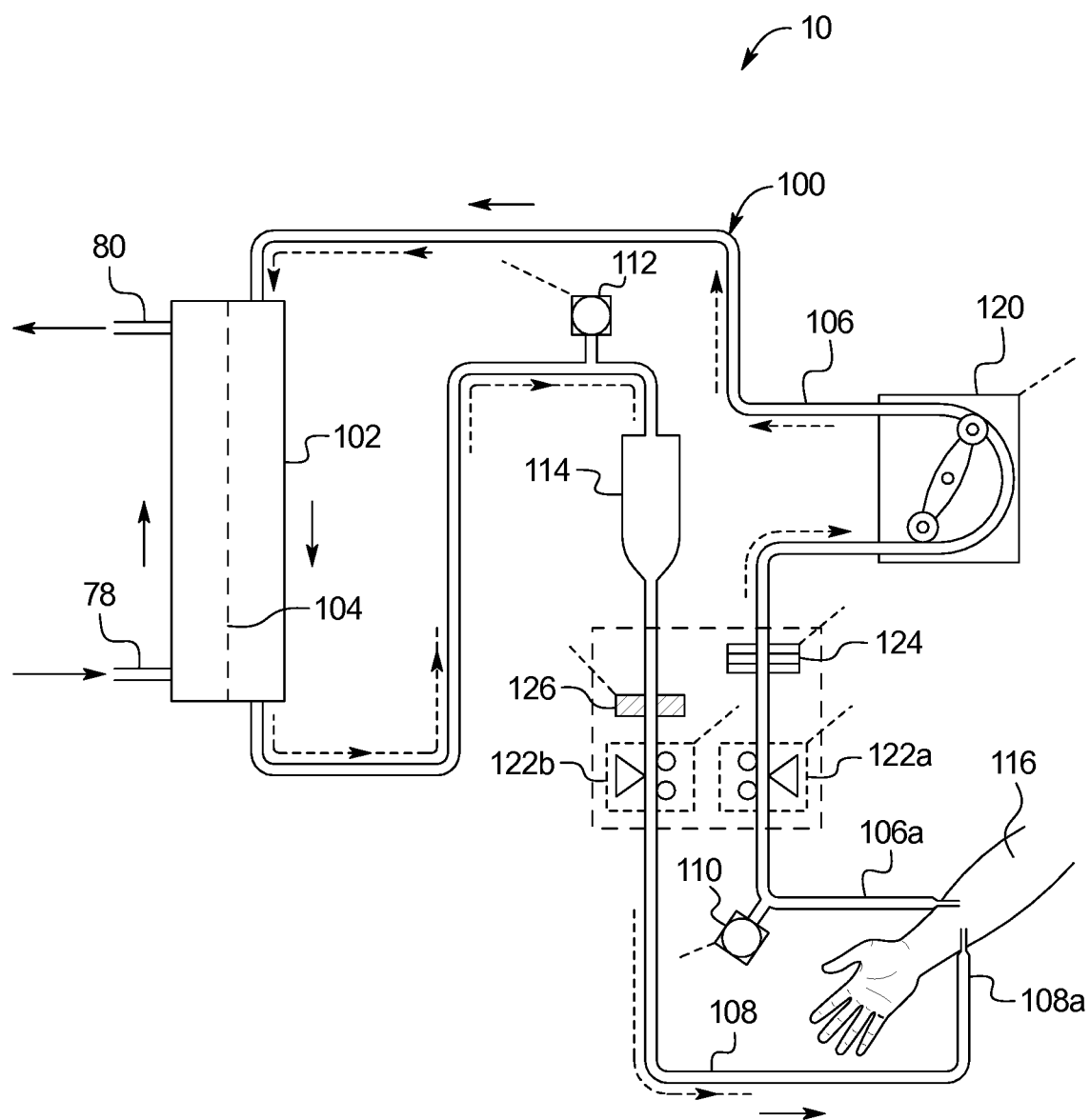
FIG. 2 is a schematic illustration of one embodiment of a blood circuit for a renal failure therapy system having a floating fluid pathway.

Referring now to the drawings and in particular to FIGS. 1 and 2, an embodiment of a system of the present disclosure is illustrated by system 10. System 10 includes a machine 12 having an enclosure or housing. The housing of machine 12 holds the contents of a dialysis fluid or dialysis fluid circuit 30 described in detail below. The housing or machine 12 also supports a user interface 14, which allows a nurse or other operator to interact with system 10. User interface 14 may have a monitor screen operable with a touch screen overlay, electromechanical buttons, e.g., membrane switches, or a combination of both. User interface 14 is in electrical communication with at least one processor 16 and at least one memory 18. At least one processor 16 and at least one memory 18 also electronically interact with, and where appropriate, control the pumps, valves and sensors described herein, e.g., those of dialysis fluid circuit 30. At least one processor 16 and at least one memory 18 are referred to collectively herein as a logic implementer 20. The dashed lines extending from logic implementer 20 lead to pumps, valves, sensors, the heater and other electrical equipment, as indicated by like dashed lines leading from the pumps, valves, sensors, heater, etc.

Dialysis fluid circuit 30 includes a purified water line 32, an A-concentrate line 34 and a bicarbonate B-concentrate line 36. Purified water line 32 receives purified water from a purified water device or source 22. The water may be purified using any one or more process, such as, reverse osmosis, carbon filtering, ultraviolet radiation, electrodeionization ("EDI"), and/or ultrafiltering.

An A-concentrate pump 38, such as a peristaltic or piston pump, pumps A-concentrate from an A-concentrate source 24 into purified water line 32 via A-concentrate line 34. Conductivity cell 40 measures the conductive effect of the A-concentrate on the purified water, sends a signal to logic implementer 20, which uses the signal to properly proportion the A-concentrate by controlling A-concentrate pump 38. The A-conductivity signal is temperature compensated via a reading from temperature sensor 42.

A B-concentrate pump 44, such as a peristaltic or piston pump, pumps B-concentrate from a B-concentrate source 26 into purified water line 32 via B-concentrate line 36. Conductivity cell 46 measures the conductive effect of the B-concentrate on the purified water/A-concentrate mixture, sends a signal to logic implementer 20, which uses the signal to properly proportion the B-concentrate by controlling B-concentrate pump 44. The B-conductivity signal is also temperature compensated via a reading from temperature sensor 48.

An expansion tank 50 deaerates the purified water prior to receiving the concentrates, removing bubbles from the water, which has been degassed in a chamber 51 via a degassing pump 53, located below expansion tank 50. A heater 52 controlled by logic implementer 20 heats the purified water for treatment to body temperature, e.g., 37° C. The fluid exiting conductivity cell 46 is therefore freshly prepared dialysis fluid, properly degassed and heated, and suitable for sending to dialyzer 102 for treatment. A fresh dialysis fluid pump 54, such as a gear pump, delivers the fresh dialysis fluid to dialyzer 102. Logic implementer 20 controls fresh dialysis fluid pump 54 to deliver fresh dialysis fluid to the dialyzer at a specified flowrate as described in more detail below.

A used dialysis fluid line 56 via a used dialysis fluid pump 58 returns used dialysis fluid from the dialyzer to a drain 60 located at the end of an external drain line 57 running between machine 12 and drain 60. Logic implementer 20 controls used dialysis fluid pump 58 to pull used dialysis fluid from dialyzer 102 at a specified flowrate. An air separator 62 separates air from the used dialysis fluid line 56. A pressure sensor 64 senses the pressure of used dialysis fluid line 56 and sends a corresponding pressure signal to logic implementer 20. Drain 60, via its piping and plumbing is connected to electrical earth grounding 28. Connection to earth ground 28 may occur directly at the drain gully. Or, if the drain's pipe system is plastic, the drain's physical contact to earth may be lower down in the drain pipe system. But due to biological film and a humid environment in the pipe system of drain 60, the impedance between machine 12 and electrical earth grounding 28 is normally not high even if the drain system includes plastic pipe for a number of meters.

Conductivity cell 66 measures the conductivity of used fluid flowing through used dialysis fluid line 56 and sends a signal to logic implementer 20. The conductivity signal of cell 66 is also temperature compensated via a reading from temperature sensor 68. A blood leak detector 70, such as an optical detector, looks for the presence of blood in used dialysis fluid line 56, e.g., to detect if a dialyzer membrane has a tear or leak. A heat exchanger 72 recoups heat from the used dialysis fluid exiting dialysis fluid circuit 30 to drain 60, preheating the purified water traveling towards heater 52 to conserve energy.

A fluid bypass line 74 allows fresh dialysis fluid to flow from fresh dialysis fluid line 76 to used dialysis fluid line 56 without contacting dialyzer 102. A fresh dialysis fluid tube 78 extends from machine 12 and carries fresh dialysis fluid from fresh dialysis fluid line 76 to dialyzer 102. A used dialysis fluid tube 80 also extends from machine 12 and carries used dialysis fluid from dialyzer 102 to used dialysis fluid line 56.

Fresh dialysis fluid line also includes a conductivity sensor or cell 82 that senses the conductivity of fresh dialysis fluid leaving a UF system 90 and sends a corresponding signal to logic implementer 20. The conductivity signal of cell 82 is likewise temperature compensated via a reading from temperature sensor 84.

An ultrafilter 86 further purifies the fresh dialysis fluid before being delivered via dialysis fluid line 76 and fresh dialysis fluid tube 78 to dialyzer 102. Alternatively or additionally, one or more ultrafilter (additional ultrafilter is not illustrated) is used to purify the fresh dialysis fluid to the point where it may be used as substitution to perform from pre- or post-dilution hemofiltration or hemodiafiltration.

UF system 90 monitors the flowrate of fresh dialysis fluid flowing to dialyzer 102 (and/or as substitution fluid flowing directly to the blood set (FIG. 2)) and used fluid flowing from the dialyzer. UF system 90 includes fresh and used flow sensors Q1c and Q2c, respectively, which send signals to logic implementer 20 indicative of the fresh and used dialysis fluid flowrate, respectively. Logic implementer 20 uses the signals to set used dialysis fluid pump 58 to pump faster than fresh dialysis fluid pump 54 by a predetermined amount to remove a prescribed amount of ultrafiltration ("UF") from the patient over the course of treatment. Fresh and used flow sensors Q1p and Q2p are redundant sensors that ensure UF system 90 is functioning properly.

System 10 provides plural valves 92 (collectively referring to valves 92a to 92f) under the control of logic implementer 20 to selectively control a prescribed treatment. In particular, valve 92a selectively opens and closes bypass line 68, e.g., to allow disinfection fluid to flow from fresh dialysis fluid line 76 to used dialysis fluid line 56. Valve 92b selectively opens and closes fresh dialysis fluid line 76. Valve 92c selectively opens and closes used dialysis fluid line 56. Valve 92d selectively opens and closes used dialysis fluid line 56 to external drain line 57 and drain 60. Valve 92e selectively opens and closes purified water line 32 to purified water source 22. Valves 92f and 92g control A- and B-concentrate flow, respectively. Valves 92h to 92k operate with UF system 90.

It should be appreciated that the dialysis fluid circuit 30 is simplified and may include other structure (e.g., more valves) and functionality not illustrated. Also, dialysis fluid circuit illustrates on example of a hemodialysis ("HD") pathway. It is contemplated to provide an additional ultrafilter (not illustrated) in fresh dialysis fluid line 76 to create substitution fluid for hemofiltration ("HF"). It is also contemplated to provide one or more ultrafilter in one or more line(s) branching off of fresh dialysis fluid line 76 to create substitution fluid, in addition to the fresh dialysis fluid in line 76, for hemodiafiltration ("HDF").

Referring now to FIG. 2, blood circuit or set 100 illustrates one embodiment of a blood set that may be used with either system 10. Blood circuit or set 100 includes a dialyzer 102 having many hollow fiber semi-permeable membranes 104, which separate dialyzer 102 into a blood compartment and a dialysis fluid compartment. The dialysis fluid compartment during treatment is placed in fluid communication with a distal end of fresh dialysis fluid tube 78 and a distal end of used dialysis fluid tube 80. For HF and HDF, a separate substitution tube, in addition to fresh dialysis fluid tube 78, is placed during treatment in fluid communication with one or both of arterial line 106 extending from an arterial access 106a and venous line 108 extending to a venous access 108a. In HDF, dialysis fluid also flows through dialysis fluid tube 78 to dialyzer 102, while for HF, dialysis fluid flow through tube 78 is blocked.

An arterial pressure pod 110 may be placed upstream of blood pump 120, while venous line 108 includes a pressure pod 112. Pressure pods 110 and 112 operate with blood pressure sensors (not illustrated) mounted on the machine housing, which send arterial and venous pressure signals, respectively, to logic implementer 20. Venous line 108 includes a venous drip chamber 114, which removes air from the patient's blood before the blood is returned to patient 116.

Arterial line 106 of blood circuit or set 100 is operated on by blood pump 120, which is under the control of logic implementer 20 to pump blood at a desired flowrate. System 10 also provides multiple blood side electronic devices that send signals to and/or receive commands from logic implementer 20. For example, logic implementer 20 commands pinch clamps 122a and 122b to selectively open or close arterial line 106 and venous line 108, respectively. A blood volume sensor ("BVS") 124 is located along arterial line 106 upstream of blood pump 120. Air detector 126 looks for air in venous blood line 108.

Referring now to FIG. 3A, an overall applied part 130 (dashed enclosure) is formed via floating fluid pathway 140. Overall applied part 130 encompasses (i) any portion of blood set 100 contacted by blood (including needle access 106a/108a shown in FIG. 3A as being combined into a central venous catheter), and any conductive components, parts or materials contacting the blood, and (ii) any portion of dialysis fluid circuit 30 contacted by a conductive fluid, e.g., dialysis fluid, liquid concentrate, and perhaps non-deionized water, and any conductive components, parts or materials contacting the dialysis fluid, liquid concentrate, and perhaps non-deionized water. Floating fluid pathway 140 accordingly includes (i) arterial line 106, venous line 108, arterial and venous needles 106a/108a (or catheter such as central venous catheter), pressure pods 110, 112, drip chamber 114, and dialyzer 102 of blood set 100, and (ii) fresh dialysis fluid line 76, fresh dialysis fluid tube 78, liquid concentrate lines 34 and 36, concentrate sources 24 and 26 if liquid concentrate sources are used, water line 32 and water source 22 if the purified water is non-deionized, used dialysis fluid tube 80, and used dialysis fluid line 56 of dialysis fluid circuit 30. External drain line 57 extends from Floating fluid pathway 140 to drain 60.

There are multiple goals of the floating fluid pathway system 10 of the present disclosure. One goal is to create and maintain a structured overall applied part 130 that tends to prevent leakage currents from entering floating fluid pathway 140 from electronic equipment located inside machine 12. A corollary to this goal is that only low voltage, signal-type components may be added to the overall applied part 130 formed via floating fluid pathway 140. A larger operating voltage pump, for example, may have a conductive fluid contacting component that becomes part of overall applied part 130. But the pump itself electrically isolates its operating voltage circuitry from its applied part fluid contacting component.

A second goal of system 10 is to force any fault voltage generated at patient 116 to be isolated in floating fluid pathway 140, i.e., to be isolated within the blood and dialysis fluid itself, leading to external drain line 57 and drain 60. Doing so increases the impedance that the fault voltage sees, so that the resulting fault current is reduced. A fault voltage generated at patient 116, for example, would travel through the blood in patient 116, the blood in arterial line 106, used dialysis fluid in tube 80, and used dialysis fluid in used dialysis fluid line 56, through external drain line 57 to drain 60. The sum of the liquid impedances to drain of the floating fluid pathway of the present disclosure is higher compared to machines currently on the market, which provide a protective earth in the fluid flow path in the machine (typically just after the dialyzer in the used dialysis fluid line). The impedance provided by the used dialysis fluid line 56 between the grounding point after dialyzer 102 for known dialysis machines and the earth ground in drain 60 is accordingly additional impedance to the impedance provided by known dialysis machines. The additional impedance of system 10 helps to reduce any current from the patient due for example to an outside failing electronic device.

FIG. 3A also introduces mechanical electrical insulation, such as insulating block 180 discussed below in connection with FIG. 6 and electrical isolation, such as electrical isolation circuit 210 discussed below in connection with FIGS. 7A to 7D. Mechanical insulation 180 is physical, non-conductive insulation, such as plastics, rubbers, ceramics, air gaps, and combinations thereof. Concerning flow components, such as components 40, 46, 66, 82 and 90, mechanical insulation 180 defines a portion of the edge of the overall applied part 130. Mechanical insulation 180 is also provided along the inner and/or outer surface of housing or machine 12 to prevent fault currents from entering the machine from the environment. Electrical isolation circuit 210 also defines a portion of the edge of overall applied part 130. Electrical isolation circuit 210 here forms a physical break in the signal or low voltage (e.g., 5 VDC) wiring from components 40, 46, 66, 82 and 90, preventing fault currents from entering overall applied part 130, e.g., from AC/DC source 132. AC/DC source 132 also has its own electrical insulation 134. Thus there are two layers of electrical insulation 134 and 210 between patient 116 and AC/DC source 132. If layer 134 fails, layer 210 remains in force and vice versa.

Current traveling in the liquids in dialysis fluid circuit 30 and blood circuit or set 100 will contact any instrumentation placed in the liquid pathways. Conductivity cells 40, 46, 66 and 82 as discussed above measure the conductivity of the fresh or used dialysis fluid and therefore may be disrupted and/or falsely indicate conductivity due to the current of a fault condition flowing through the fresh or used dialysis fluid. Additionally, flow sensors Q1c, Q2c, Q1p, and Q2p of UF system 90 may be electromagnetic flow sensors. Electromagnetic flow sensors in general apply a magnetic field to the dialysis fluid circuit 30 tubing, which results in a potential difference proportional to a flow velocity perpendicular to the flux lines of the field. Magnetic flow meters or sensors typically require a conducting fluid, such as dialysis fluid. Therefore again, the presence of a current due to an internal machine 12 component fault or an external fault or disturbance at patient 116 conducting through the fresh or used dialysis fluid may disrupt the operation of the magnetic flow sensors and/or cause them to indicate a false flowrate.

Conductivity sensors and flow sensors mentioned above are susceptible to error due to eddy currents in their respective flow paths because they measure a voltage over a part of the flow path. Sensors that do not, such as blood leak detectors (optical) and temperature sensors, which measure voltage or current but not over a portion of the flow path, are less susceptible to fault or eddy current error.

System 10 in FIG. 1 illustrates electrical bypasses 150a to 150e and 150g, which provide short circuit pathways around each of the electrically sensitive conductivity cells 40, 46, 66 and 82 and sensitive flow sensors Q1c, Q2c, Q1p, and Q2p of UF system 90. Conductivity cells 40, 46, 66 and 82 and sensitive flow sensors Q1c, Q2c, Q1p, and Q2p of UF system 90 are examples of electrical components sensitive to electrical disturbances, whose conductivity and flowrate readout signals may be impacted by stray or fault currents flowing within the fresh or used dialysis fluid, potentially creating inaccuracy. Electrical bypasses 150a to 150e and 150g cause a current due to a fault condition flowing through the fresh or used dialysis fluid to flow instead through the bypasses, allowing the sensitive equipment to operate correctly and to readout accurately. In FIGS. 1 and 4A to 4C, the electrical lines for bypasses 150 (referring to each of bypasses 150a to 150f) are illustrated as dashed lines to distinguish them from the blood and dialysis fluid lines, which are illustrated as solid lines.

Because one goal of the present disclosure is to increase the impedance seen by any fault current emanating from patient 116, it is desirable to minimize the length of bypasses 150, which provide effectively zero impedance over their lengths. Consequently, the connections of bypasses 150 should be kept in the proximity of the component within the fluid path to be bypassed or shortcut to keep the impedance of the fluid path as high as possible.

While five bypasses 150a to 150e and 150g are illustrated for the sensitive components, system 10 may have any number of bypasses required to bypass all sensitive equipment that may be affected by a current due to a fault condition flowing through the fresh or used dialysis fluid. In FIG. 2, the dotted line illustrates generally the stray current path for a fault current entering blood circuit 100 along arterial line 106. The path extends through dialyzer 102, venous line 108, patient 116, arterial line 106, back out through dialyzer 102, and to used dialysis fluid or drain line 56.

When, as in FIGS. 1 to 3, there is one common floating fluid pathway 140 for both fresh dialysis fluid and used dialysis fluid, a short circuit bypass 150f (FIG. 1) may be provided between fresh dialysis fluid line 76 and used dialysis fluid line 56. Fresh-spent bypass 150f as indicated by the dotted line bypasses blood circuit or set 100, dialyzer 102 and patient 116 and thereby shunts fault current in fresh dialysis fluid line 76 away from the patient, flowing instead through bypass 150f, used dialysis fluid line 56, external drain line 57 to drain 60. The relatively significant impedance in blood set 100 will ensure that the bulk of the fault current travels through the shortcut 150f, while only a small part of the fault current will take the way through the patient. Short circuit bypass 150f also helps to ensure that no eddy currents from the flow paths will flow into the inside of machine 12. Reducing eddy currents inside the machine helps to protect the operation of the sensors, such as the conductivity and flow sensors located inside the machine.

It is desirable in one aspect to place fresh-spent bypass 150f as close to dialyzer 102 as possible to shunt protect as much of fresh dialysis fluid line 76 and used dialysis fluid line 56 as possible. It is also desirable as illustrated in FIG. 1 to place fresh-spent bypass 150f within the housing or machine 12, so that the bypass is unseen and protected. Further, placing fresh-spent bypass 150f within the housing or machine 12 preserves the high impedance between machine 12 and patient 116, which is desirable as discussed in detail below to reduce the amount of fault current that may be generated within the floating fluid pathway.

A conductive bypass may be provided alternatively using the conductive dialysis fluid flowing through fluid bypass line 74. As illustrated, fluid bypass line 74 includes bypass valve 92a, which is normally closed during treatment. It is contemplated to choose or make the housing, stem, ball, plunger and/or seat of bypass valve 92a metal or otherwise conductive (e.g., carbon), so that the conductive housing, stem, ball, plunger and/or seat of bypass valve 92a helps to shunt fault or eddy currents through external drain line 57 to drain 60.

Referring now to FIG. 3B, a schematic diagram showing estimated or example impedances for system 10 including floating fluid pathway 140 through dialysis fluid circuit 30 and blood set 100 having bypasses 150 (referring collectively to bypasses 150a to 150f) is illustrated. FIG. 3B addresses instances in which (i) a fault occurs at patient 116 due to an external potential/voltage source (including AC or DC) indicated as X volt 105, which may be generated, for example, if the patient uses a computer with faulty power cord insulation, or (ii) a fault occurs in water line 32 or dialysis fluid lines 76 or 56, such that floating fluid pathway 140 includes dialysis fluid circuit 30, blood circuit or set 100, dialyzer 102 and patient 116. A fault may occur in fresh or used dialysis fluid lines 76/56, for example, due to a faulty wiring connection to one of its fluid components.

The impedances discussed in connection with FIG. 3B are approximate and may vary but are illustrative of common scenarios. For example, the 30 kOhms and 100 kOhms of FIG. 3B are approximate representations of the total resistance or impedance provided by conductive fluid in blood set 100 and/or dialysis fluid circuit 30 of system 10. From patient 116 to dialyzer 102, impedances approximated at 30 kOhms in both arterial line 106 and venous line 108 add in parallel and produce a total resulting approximate impedance of about 15 kOhms (30 kOhms may be a worst case condition from the standpoint that blood pump 120 may initially contribute an impedance significantly higher than 30 kOhms, but over treatment lower in impedance due to wearing and tearing of the insulation of blood pump 120). Used dialysis fluid tube 80 presents an approximated 30 kOhms of impedance. Used dialysis fluid line 56 within machine 12 presents an approximated 100 kOhms of impedance. External drain line 57 between the housing of machine 12 and drain 60 presents another approximated 100 kOhms of impedance. The overall approximate impedance between patient 116 and drain 60 is thus (15+30+100+100) 245 kOhms. If bypass line 150f is provided as illustrated and described in connection with FIG. 1, then there are two parallel paths placed in series with used dialysis fluid line 56, namely, (1/30+1/30=1/resistance from patient 116 to dialyzer 102=15 kOhms)+(1/30+1/30=1/resistance from dialyzer 102 to used dialysis fluid line 56=15 kOhms), so that the overall approximate impedance between patient 116 and drain 60 is reduced to (100+100+15+15) 230 kOhms.

In known machine designs where components that contact the dialysis fluid are in direct contact with protective earth, the resistance from the patient towards protective earth is typically only 30 kOhms. If for example, a minor faulty component generates a smaller voltage between protective earth of only 12 VDC, this smaller voltage may drive a current of 12 VDC/30,000 Ohms=400 microamperes with known machines. With the floating fluid pathways of system 10 (assuming 245 kOhms as set forth in the above example), the same faulty voltage (12 VDC) will generate a current of only 12 VDC/245000 Ohms=49 microamperes. If a central venous catheter is used, which is of heightened concern due to its proximity to the patient's heart and the risk of current conducting near the heart, a current limit of ten (10) to fifty (50) microamperes (0.00001 to 0.00005 Amps) may be applied. It should therefore be clear that system 10 may reduce the current due to minor faults or disturbances close to or below the accepted limit for central venous catheters, which is highly advantageous over known machines.

Figure 4A:
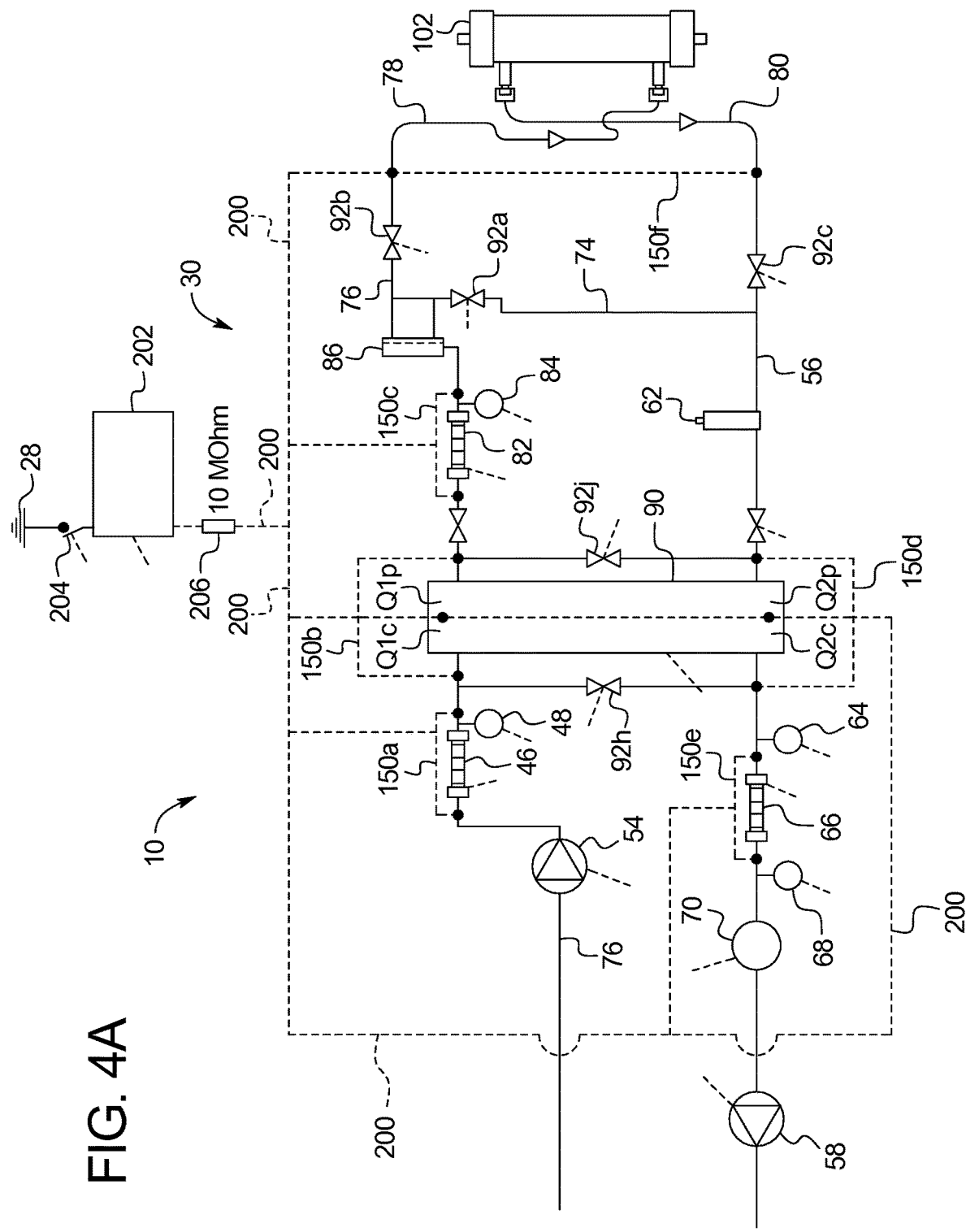
FIG. 4A is a schematic illustration showing a portion of the dialysis fluid circuit of FIG. 1 in more detail to illustrate one embodiment for a testing apparatus for the floating fluid pathway of the present disclosure.
Figure 4B:
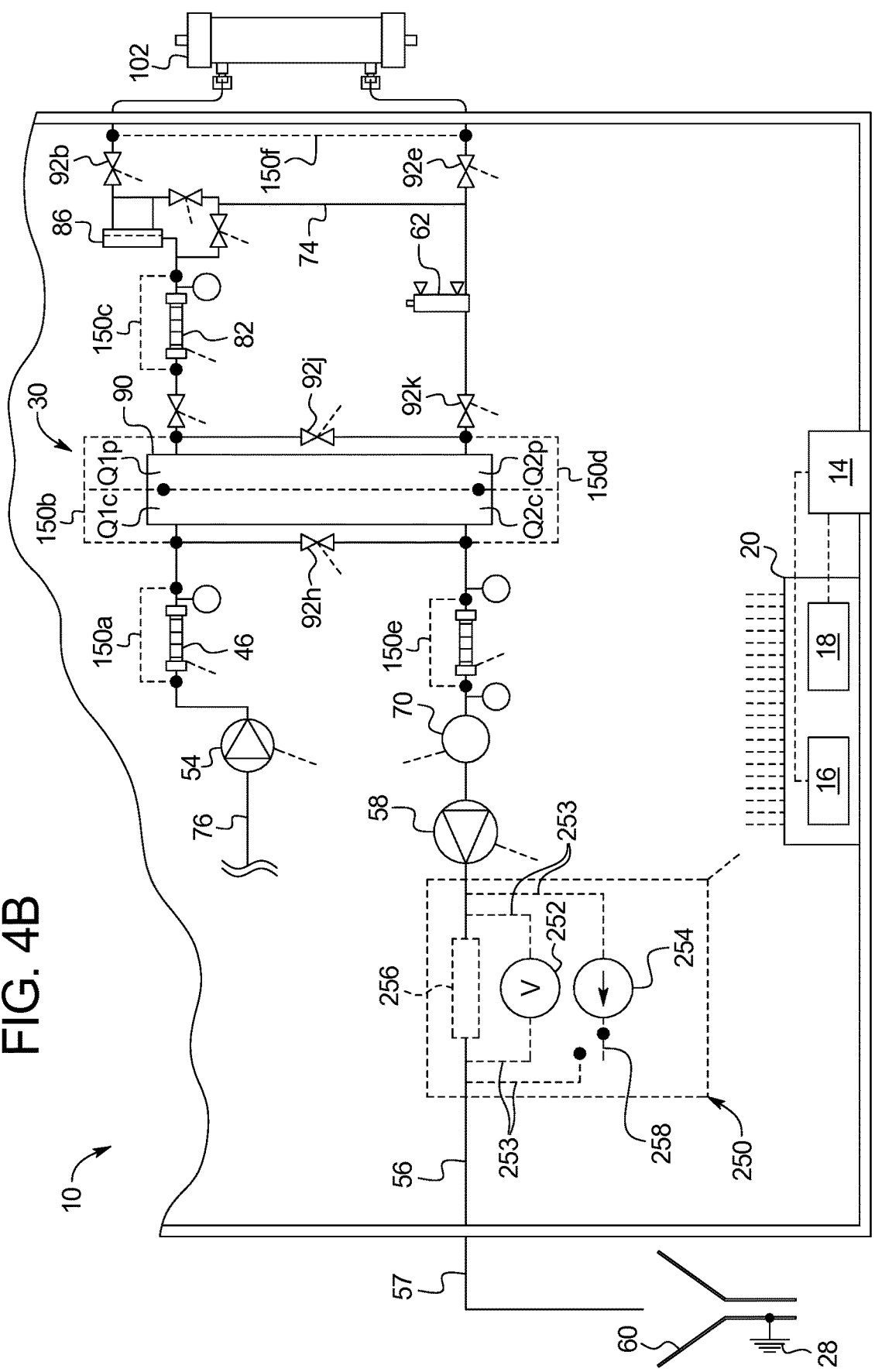
FIG. 4B is a schematic illustration showing a portion of the dialysis fluid circuit of FIG. 1 in more detail to illustrate another embodiment for a testing apparatus for the floating fluid pathway of the present disclosure.
Figure 4C:
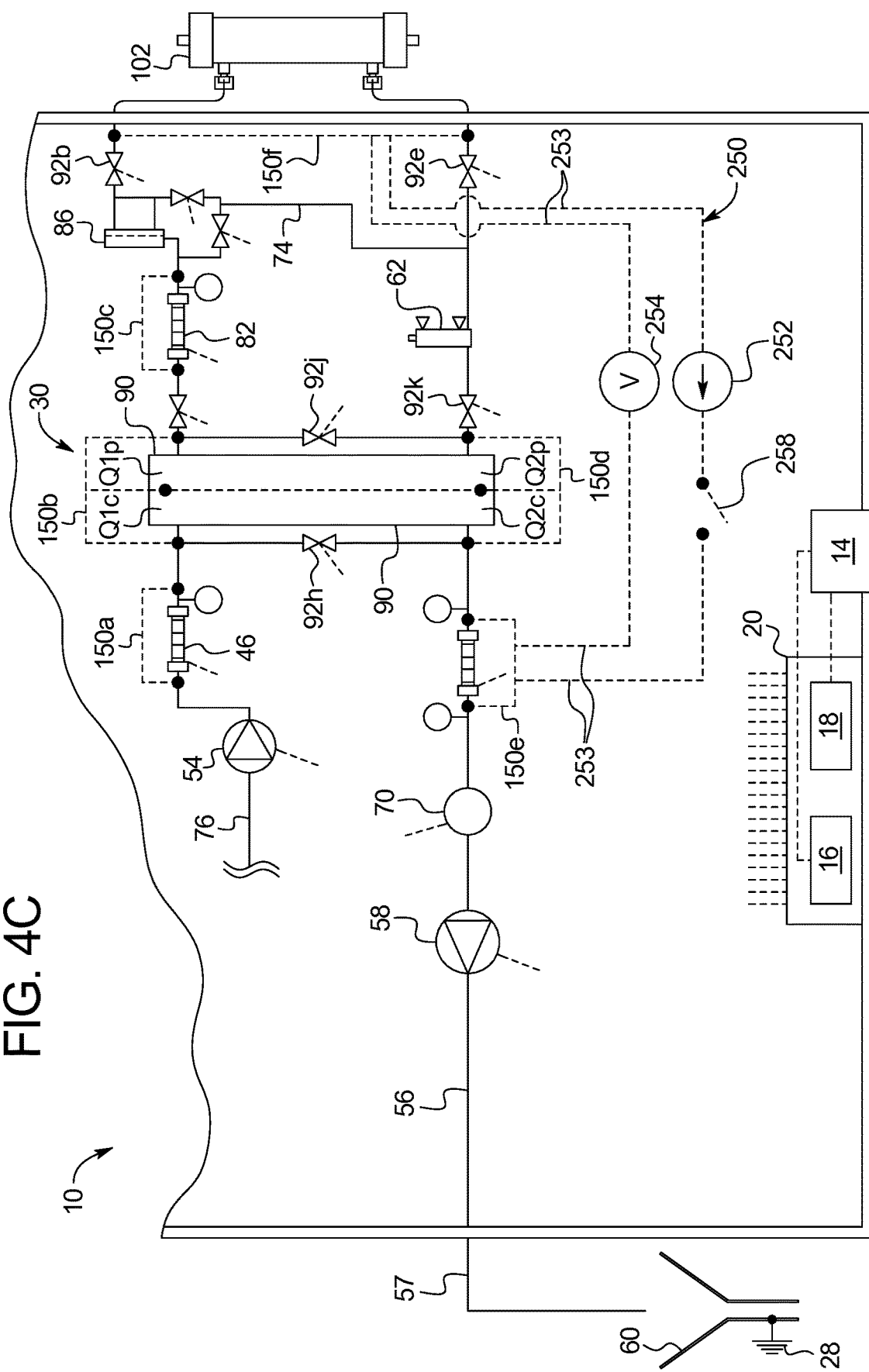
FIG. 4C is a schematic illustration showing a portion of the dialysis fluid circuit of FIG. 1 in more detail to illustrate another embodiment for a testing apparatus for the floating fluid pathway of the present disclosure.

Referring now to FIG. 4A, a portion of the dialysis fluid circuit 30 of FIG. 1 is illustrated in more detail. Like element numbers are reused, and FIG. 4A includes, even though it does not show, all of the structure, functionality and alternatives discussed above in connection with FIG. 1. In FIGS. 4A to 4C, additional electrical paths or lines 200 (FIG. 4A) and 253 (FIGS. 4B and 4C) and electrical lines of bypasses 150 (referring collectively to bypasses 150a to 150f) are illustrated as dashed lines to distinguish same from the solid fluid lines.

FIG. 4A illustrates a feedback embodiment for floating fluid pathway 140 and bypasses 150 of system 10 described herein. This embodiment shows one example of how to test the integrity of the floating fluid pathway system 10 outside of treatment and before the patient is connected to machine 12. This test may be performed for example during a functional check of machine 12 or during a so-called priming procedure for blood set 100 when the patient is not connected to the machine. FIG. 4A illustrates that system 10 provides current meter 202 connected to electrical line 200, which in turn is connected electrically to one, or more, or each of bypasses 150a to 150f. Dashed line 200 in FIG. 4A is illustrated as being connected to all bypass connections 150. In alternative embodiments, variations of FIG. 4A may be provided, one of which connects dashed line 200 to only one of the bypass lines 150 (e.g., at bypass line 150f extending between valve 92b and valve 92c). Further alternatively, conductive test points not directly linked to bypass lines 150 may be added, or any combination of directly connected test lines 200 and not directly connected test lines 200 may be provided.

Figure 5A:
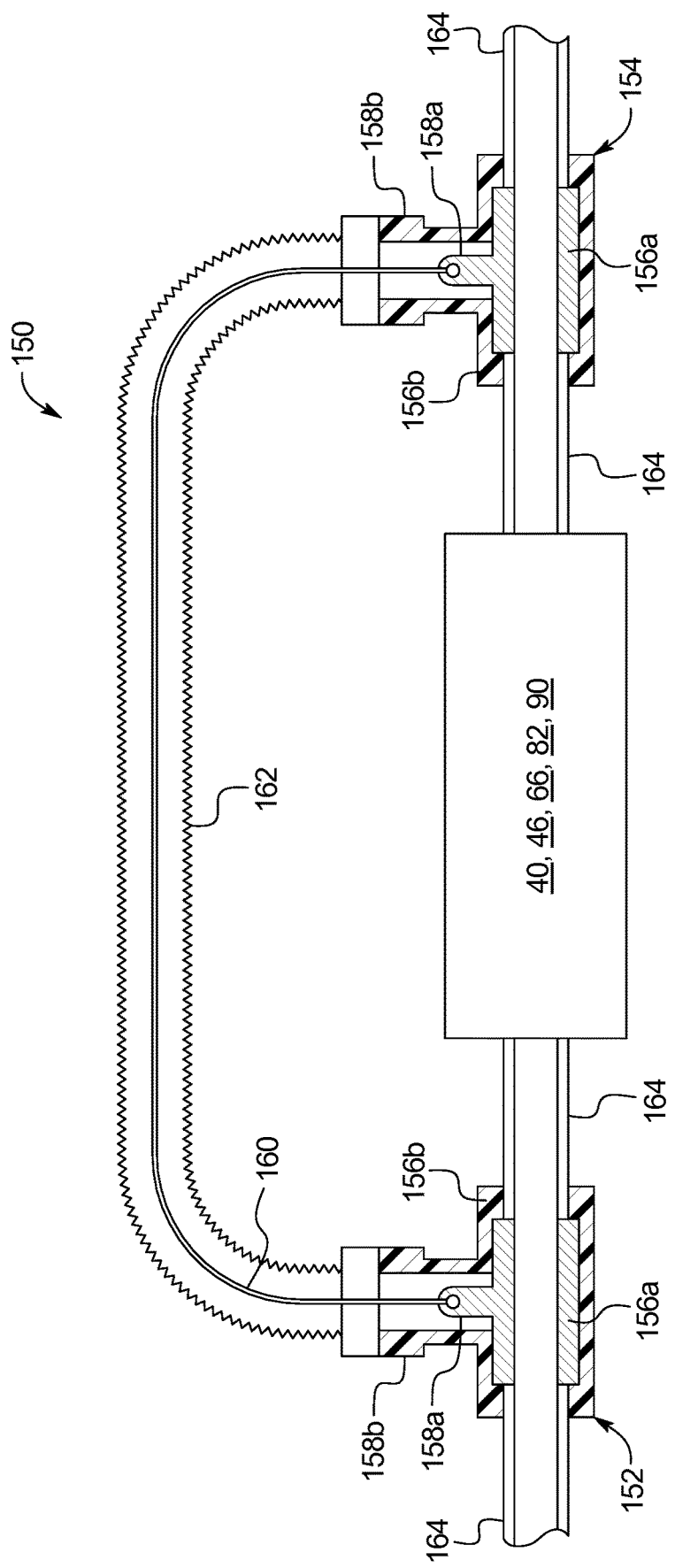
FIG. 5A is side sectioned view of one embodiment for an electrical bypass of the present disclosure.

FIG. 5A below illustrates conductive couplers 152 and 154 having conductive portions 156a, which may provide one or more additional port for receiving electrical line 200, enabling electrical path or line 200 to be connected to a conductive tee 158a or to wire or conductor 160 located within bypasses 150. In FIG. 4A, current meter 202 is connected via a switch 204 to earth ground 28 (this is the same ground that might exist in drain 60 or that the patient may contact by touching an electrical lamp that is grounded). Drain 60 in FIG. 1 is also grounded to earth ground 28. Current meter 202 and switch 204 are electrically connected to and are under the control of logic implementer 20. In one example, a resistor 206, such as a larger resistor in the megaOhm range, may be placed in between electrical path or line 200 and current meter 202.

When logic implementer 20 closes switch 204, any fault current may flow to earth ground 28 via electrical line path or 200 and resistor 206. Current meter 202 measures any such current. If floating fluid pathway system 10 has its integrity in place, current meter 202 measures no current or a very small current, which logic implementer 20 reads and determines that treatment may proceed. If the measured current is too high, e.g., above a preset threshold of for example ten to fifty microamperes (10 to 50 µA), then logic implementer 20 determines that floating fluid pathway 140 has been compromised and sounds and/or displays an audio, visual or audiovisual alarm at user interface 14. The nurse or clinician may then prevent a treatment from beginning and patient 116 from connecting to machine 12. Again, in an embodiment, the feedback and testing associated with FIG. 4A is performed while machine 12 is full of fluid but before patient 116 is connected to machine 12, e.g., during filling or priming.

Logic implementer 20 may be programmed with safeguards against false trips or oversensitivity. In various examples, logic implementer 20 may be programmed to detect the current measured by current meter 202 and compare it to a threshold, e.g., to be above the threshold current level for a certain amount of time, and/or to compute an average or filtered current output and determine if such output rises above the current threshold instantaneously or for a certain amount of time. Such safeguards protect against inadvertent current spikes, which may otherwise wrongfully halt a treatment.

Switch 204 may be closed before and/or after treatment, e.g., during priming or disinfection, so that any current sensed by current meter 202 does not flow to the patient. In such a case, the resistance of resistor 206 may be low or even eliminated, causing the current sensed at current meter 202 to be more robust. Providing a high resistance resistor 206 in an alternative embodiment enables the feedback structure of FIG. 4A, including current meter 202, switch 204 and the resistor to test floating fluid pathway 140 during treatment, because even a relatively high fault voltage will produce a small current to earth ground 28 via resistor 206. For example, a 240 Volt fault voltage using a ten megaOhm resistor for example would produce only a 0.000024 Amp (24 microamperes) current, 240 Volts÷10,000,000 Ohms=0.000024 Amps, which is below a fifty (50) microampere (0.00001 to 0.00005 Amps) limit for treatment with central venous catheters. It is contemplated for logic implementer 20 to cause an audio, visual or audiovisual alarm to be provided during treatment, so that the nurse or clinician may shut down the treatment and disconnect patient 116 from machine 12.

It is contemplated for logic implementer 20 to cause an audio, visual or audiovisual alarm to be provided during treatment if the measured current meets or exceeds a preset threshold. Logic implementer 20 may then place machine 12 into a patient safe state, allowing the nurse or clinician to shut down treatment and disconnect patient 116 from machine 12. This in-treatment test may have some drawbacks, including that the patient is exposed to earth ground 28 even with the large resister, and that the current sensed will likely be very small, which may be difficult.

Referring now to FIG. 4B, one preferred in-treatment test embodiment is illustrated. In FIG. 4B, a portion of the dialysis fluid circuit 30 of FIG. 1 is illustrated in more detail. Like element numbers are reused, and FIG. 4B includes, even though it does not show, all of the structure, functionality and alternatives discussed above in connection with FIG. 1. In FIG. 4B, dialysis fluid circuit 30 also includes a leakage current measuring device 250. Leakage current measuring device 250 includes or uses a voltage meter 252 and a current generator 254, which are both placed in electrical communication via electrical lines 253 with a flow path resistance 256. Flow path resistance 256 may be any portion or all of the fluid within fresh dialysis fluid line 76, used dialysis fluid line 56, bypass line 74, and/or any line within blood set 100. Voltage meter 252 and current generator 254 may be placed into electrical communication with the fluid of flow path resistance 256 via couplers 152 and 154 discussed below in one embodiment.

Alternatively, two or more leakage current measuring devices 250 may be employed, for example, one leakage current measuring device 250 in fresh dialysis fluid line 76 just upstream of dialyzer 102 and another leakage current measuring device 250 located in used dialysis fluid line 56 just downstream from dialyzer 102. Logic implementer 20 may receive signals from both fresh and used leakage current measuring devices 250 and react as described below if either leakage current measuring device 250 reads too high a fault current or voltage.

Current generator 254 is placed in electrical series with a switch 258. Switch 258 in the illustrated embodiment is a two position switch, which is either opened or closed. When closed, switch 258 injects a current into flow path resistance 256, which generates a voltage sensed by voltage meter 252. In one embodiment, logic implementer 20 may be programmed such that prior to treatment, switch 258 is closed and current generator 254 is caused to inject a current equal to an allowable limit for a desired machine rating, e.g., for a for operation with a central venous catheter. For example, logic implementer 20 may be programmed to cause current generator 254 to inject a current of fifty microamperes into flow path resistance 256. Voltage meter 252 reads the voltage generated by the fifty microamperes and sends the reading to logic implementer 20, which is stored for treatment.

After the fifty microampere voltage reading, logic implementer 20 before treatment causes switch 258 to open, such that during treatment no current conducts from current generator 254 into flow path resistance 256. During treatment however, voltage meter 252 still attempts to detect a voltage in flow path resistance 256 due to a fault or stray current, indicating that the floating fluid pathway 140 of system 10 is not working properly or cannot handle the level of the fault or stray current. In particular, logic implementer 20 in one embodiment determines if any voltage reading from meter 252 during treatment exceeds the stored fifty microampere (or other) voltage reading. If not, logic implementer 20 allows treatment to proceed. If the voltage reading from meter 252 during treatment exceeds the stored fifty microampere (or other) voltage reading, logic implementer 20 places machine 12 in a safe state, shuts down treatment and causes an audio, visual or audiovisual alarm as has been described herein.

As illustrated in FIG. 1, there is an air gap between the end of external drain line 57 and drain 60. During treatment, there is a continuous flow of used dialysis fluid to drain 60 in the air gap, such that stray or fault currents have a path to earth ground 28 via drain 60. But once used dialysis fluid flow stops due to the machine being shutdown after the alarm, the air gap opens, breaking any path to earth ground 28, and increasing patient safety. Thus even if the patient is connected to a faulty equipment as indicated by X volt 105 in FIG. 3B, any current conducting through the patient's heart will be halted within a short period of time. Dialysis fluid flow within dialysis machine 12 may be stopped within less than 100 milliseconds ("ms") from the time logic implementer determines that an integrity issue exists.

While current measuring device 250 is described as having a voltage meter 252 and a current generator 254, measuring device 250 may alternatively include a current meter and a voltage generator. Another possible variation of system 10 of FIG. 4B is to provide or assume a predetermined resistance for flow path resistance 256. Here, the need for the test before treatment may be avoided, and thus current generator 254 and switch 258 are not needed.

Referring now to FIG. 4C, another preferred in-treatment test embodiment is illustrated. In FIG. 4B, like with FIG. 4C, a portion of the dialysis fluid circuit 30 of FIG. 1 is illustrated. Like element numbers are reused, and FIG. 4C includes, even though it does not show, all of the structure, functionality and alternatives discussed above in connection with FIG. 1. In FIG. 4C, like with FIG. 4B, dialysis fluid circuit 30 also includes one or more leakage current measuring device 250. Leakage current measuring device 250 again includes a voltage meter 252 (or current meter) and a current generator 254 (or voltage generator), which are both placed in electrical communication via electrical lines 253, here with plural fluid-contacting bypasses 150 (referring collectively to bypasses 150a to 150f), but alternatively with separate conductive couplers contacting the relevant fluid. In the illustrated embodiment, electrical lines 253 are connected to and between electrical bypasses 150e and 150f, which is one preferred location because of the close proximity to dialyzer 102. Electrical lines 253 may similarly be connected to and between electrical bypasses 150c and 150f. In another alternative embodiment, electrical lines 253 for a first leakage current measuring device 250 are connected to and between electrical bypasses 150e and 150f, while electrical lines 253 for a second leakage current measuring device 250 are connected to and between electrical bypasses 150a and 150c. In a further alternative embodiment, electrical lines 253 for a first leakage current measuring device 250 are connected to and between electrical bypasses 150d and 150f, while electrical lines 253 for a second leakage current measuring device 250 are connected to and between electrical bypasses 150b and 150c. Electrical lines 253 of leakage current measuring device 250 may be connected between any combinations of bypasses 150a to 150f.

Leakage current measuring device 250 in an embodiment operates as described above in connection with FIG. 4B. That is, current generator 254 is placed again in electrical series with a switch 258. When closed, switch 258 injects a current into bypasses 150 and the fluid flowing between the bypasses 150, which generates a voltage sensed by voltage meter 252. In one embodiment, logic implementer 20 may be programmed such that prior to treatment, switch 258 is closed and current generator 254 is caused to inject a current equal to an allowable limit for a desired rating, e.g., for use with a central venous catheter, such as fifty microamperes, into the wiring of bypasses 150 and the interconnecting fluid passage. Voltage meter 252 again reads the voltage generated by the fifty microamperes and sends the reading to logic implementer 20, which is stored for treatment.

After the fifty microampere voltage reading, logic implementer 20 before treatment causes switch 258 to open, such that during treatment no current conducts from current generator 254 into the wiring of bypasses 150 and the interconnecting fluid passage. During treatment however, voltage meter 252 still looks for a voltage across the bypasses 150 and the interconnecting fluid passage due to a fault or stray current, indicating that the floating fluid pathway 140 of system 10 is not working properly or cannot handle the level of the fault or stray current. Logic implementer 20 may again look to see if any voltage reading from meter 252 during treatment exceeds the stored voltage reading calculated from the applied fifty microamperes. If the stored threshold voltage reading is not met or exceeded, logic implementer 20 allows treatment to proceed. If the voltage reading from meter 252 during treatment meets or exceeds the stored voltage reading calculated from the fifty microampere applied current, logic implementer 20 places machine 12 in a safe state, shuts down treatment and causes an audio, visual or audiovisual alarm as has been described herein.

Referring now to FIG. 5A, one embodiment for implementing bypasses 150 is illustrated. Each bypass 150 may include first and second conductive couplers 152 and 154, respectively. Conductive couplers 152 and 154 may include a conductive inner portion 156a that contacts the fluid (dialysis fluid or blood) and an outer portion 156b, preferably of an insulating material to prevent external voltages from being applied through couplers 152 and 154 into the flowing fluid. Conductive inner portion 156a may be a medically safe metal, such as stainless steel, titanium, carbon, or a conductive polymer, such as carbon impregnated rubber or plastic. Conductive inner portion 156a is alternatively a conductive polymer, such as polymer containing carbon particles.

Conductive inner portion 156a and an insulating outer portion 156b each include a tee 158a and 158b, respectively. Tee 158a allows a wire or conductor 160 to be connected electrically with conductive inner portion 156a. Tee 158b allows an insulating electrical conduit 162 to be coupled to insulating outer portion 156b. Insulating outer portion 156b may also be provided with compression fittings (not illustrated) to couple to fluid (dialysis fluid or blood) conduits 164. Conductive inner portions 156a of conductive couplers 152 and 154 and wire or conductor 160 form the short circuit path (i) around sensitive component 40, 46, 66, 82 and 90 for bypasses 150a to 150e and 150g and (ii) between fresh dialysis fluid line 76 and used dialysis fluid line 56 for bypass 150f.

Figure 5B:
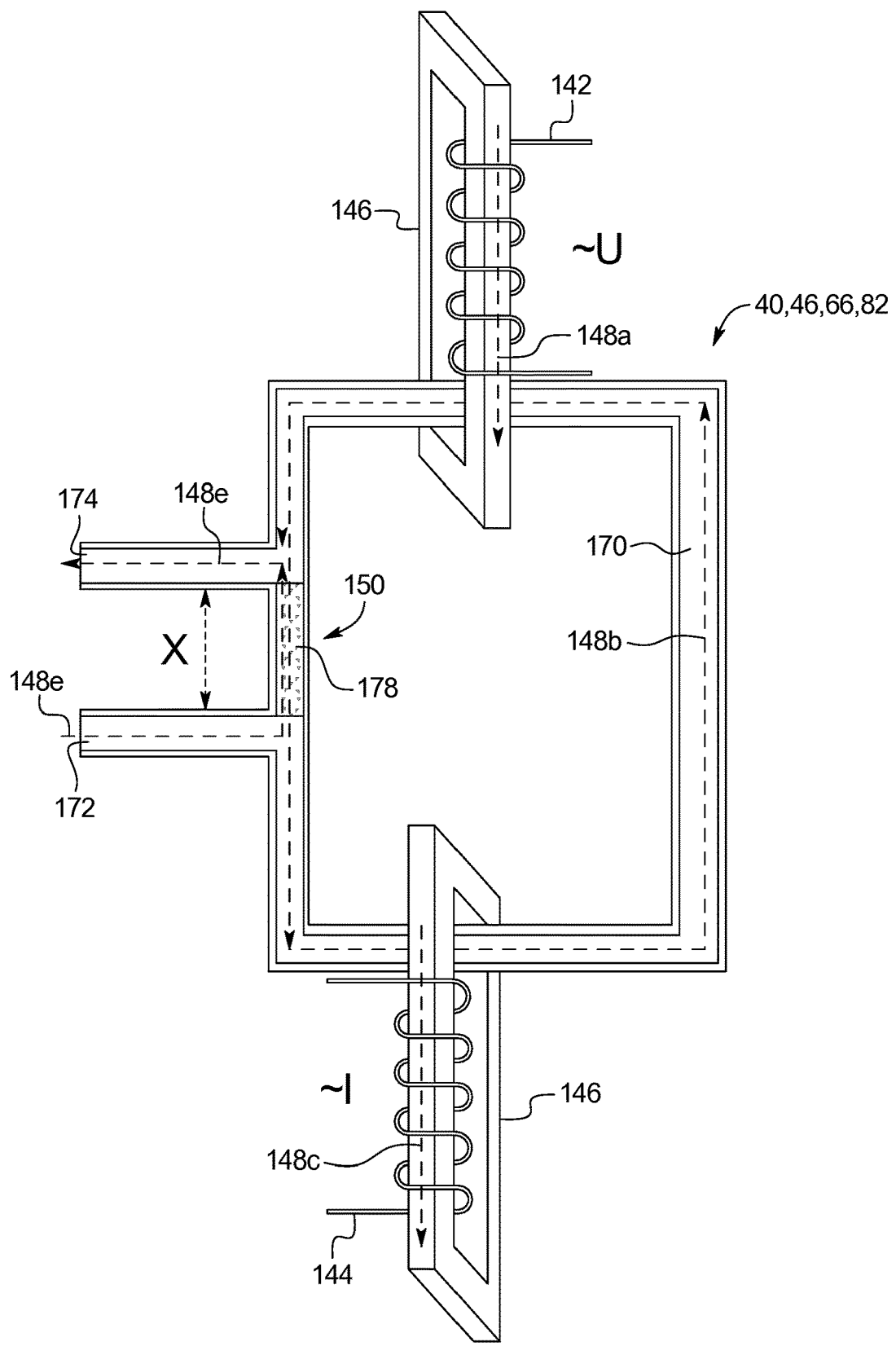
FIG. 5B is a schematic view for another embodiment of an electrical bypass of the present disclosure.

Bypass 150 of FIG. 5A is just one example bypass. The bypass may alternatively be integrated into the housings and/or circuitry of sensitive component 40, 46, 66, 82 and 90. FIG. 5B illustrates one such example.

FIG. 5B illustrates conductivity sensors or cells 40, 46, 66, and 82 in more detail. In the illustrated embodiment, conductivity sensors or cells 40, 46, 66, and 82 are of a type that operate with two coils 142, 144, each coil having an iron core 146, wherein first coil 142 is caused to emit a voltage U that induces a magnetic field (arrow 148a) in core 146, which in turn induces a desired current (arrow 148b) in a conductive fluid, such as dialysis fluid, which in turn induces a magnetic field (arrow 148c) in core 146 of second coil 144, which in turn yields a resulting current I in a sensing circuit attached to the sensing coil 144. Sensed current I depends upon the conductivity of fluid flowing through a toroid fluid path 170, which includes an inlet 172 and an outlet 174.

A problem with the type of conductivity sensor illustrated in FIG. 5B is that the sensor may be disturbed by a stray current through the sensor (arrow 148d) coming from a stray current in the main flow path (arrow 148e). Stray current through the sensor (arrow 148d) will induce an overlaying signal onto the signal provided by inducing voltage U, resulting in inaccuracy. In one solution illustrated by FIG. 5B, a conductive element 178 is placed between inlet 172 and outlet 174.

Conductive element 178 is made of an electrically conductive and medically safe material, such as, stainless steel, carbon, platinum, titanium, and combinations and alloys thereof. Conductive element 178 is made alternatively of a medically safe conductive plastic, such a medically safe plastic infused with conductive particles made of any of the materials just listed. Conductive element 178 may be a separate piece that is press-fitted into flow path 170 between inlet 172 and outlet 174. Conductive element 178 in an alternative embodiment is molded as a conductive part of flow path 170. Here, two different plastics may be used, in which one part of the molded product has a conductive plastic, while the other part of the molded product has a non-conductive plastic. Conductive element 178 may be part of sensor 40, 46, 66, and 82 itself, or be part of an add-on piece fluidically sealed between the sensor and the main flow path.

The electrical resistance of conductive element 178 is much less than that of flow path 170. The length X of conductive element 178 may also be made to be small, so that the distance between inlet 172 and outlet 174 is minimized. Both factors promote the flow of stray current (arrow 148e) directly from inlet 172 to outlet 174 as opposed to flowing all the way around the more electrically resistive flow path 170. Importantly, the low electrical resistance of conductive element 178 ensures a strong toroid of desired current flow (arrow 148b) around flow path 170 for proper sensing.

Figure 5C:
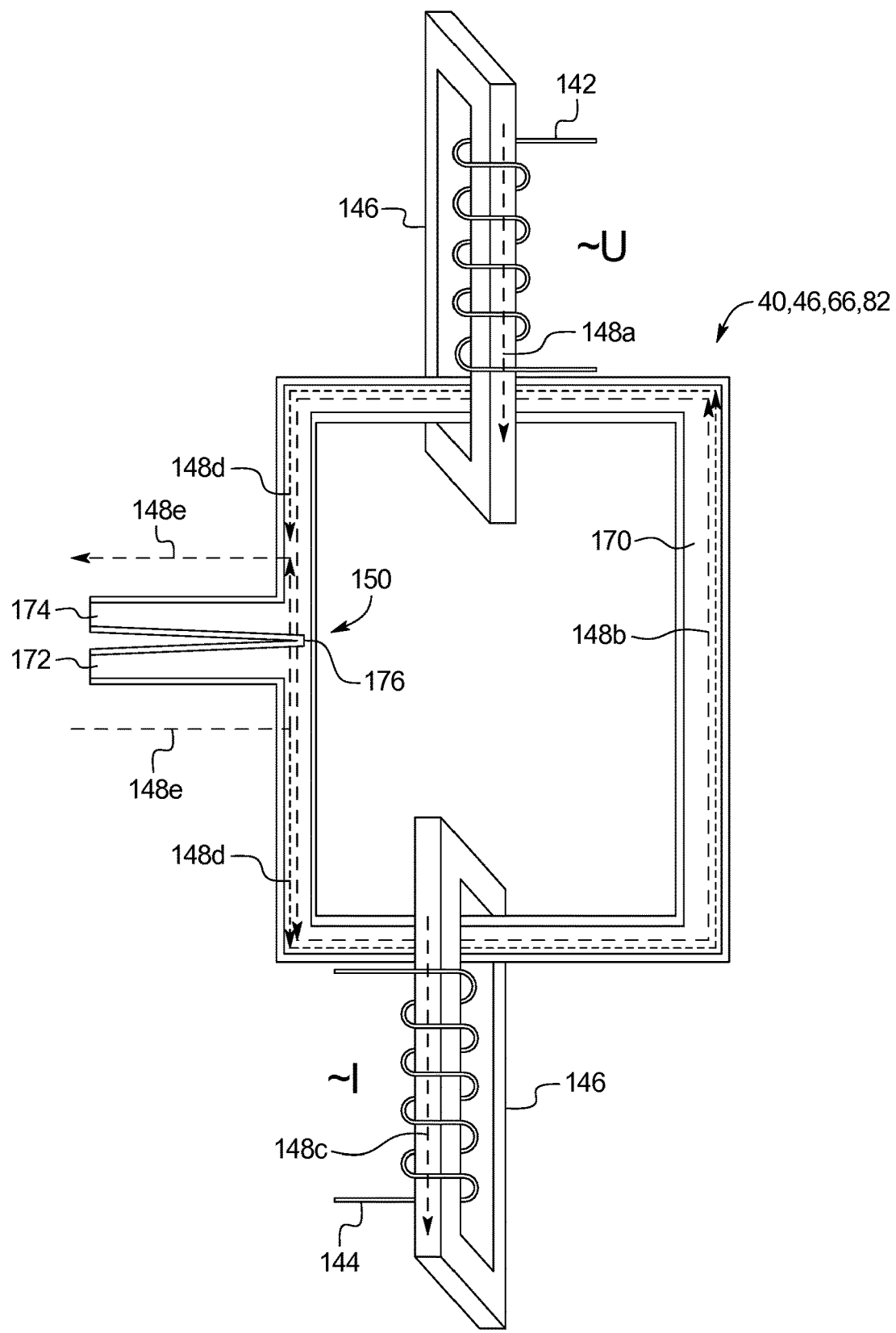
FIG. 5C is a schematic view for a further embodiment of an electrical bypass of the present disclosure.

FIG. 5C illustrates an alternative bypass 150 embodiment for the same type of conductivity sensor or cell 40, 46, 66, and 82, which includes first coil 142, second coil 144, each having an iron core 146 operating with a fluid flow path 170 having an inlet 172 and an outlet 174, wherein a desired current (arrow 148b) is promoted, while a stray current (arrow 148e) flowing through flow path 170 is minimized as much as possible. Here, instead of using conductive element 178 (FIG. 5B), bypass 150 of FIG. 5C attempts to solve the stray current problem by bringing inlet 172 and outlet 174 together using a fluid flow restrictive aperture.

FIG. 5C illustrates that inlet 172 and outlet 174 come together at a small passage 176 through which the current and the fluid can flow. The small cross-sectional area created by passage 176 will restrict fluid flow (proportional to $r^4$) far more than the restriction to electrical current flow (proportional to $r^2$). Stray current through the sensor (arrow 148d) is therefore minimized because the stray current in the main flow path (arrow 148e) is encouraged to flow directly from inlet 172 to outlet 174 (or vice versa), as opposed to flowing all the way around fluid path 170 of conductivity sensor or cell 40, 46, 66, and 82, where it may corrupt the current I induced at sensing coil 144. Conversely, small passage 176 does not allow much fluid to pass through. Thus toroid flow needed for the operation of certain types of conductivity sensors or cells 40, 46, 66, and 82 is maintained. It is believed that the majority of the stray electrical current (e.g., more than 90%) will travel through small passage 176, while only a small part of the fluid flow will travel through the same small passage (e.g., less than 10%). Small passage 176 may be part of sensor 40, 46, 66, and 82 itself or be provided as part of an add-on piece sealed fluidically between the sensor and the main flow path.

One advantage of bypass 150 of FIG. 5C versus bypass 150 of FIG. 5A is that an important resistance associated with conductive element 178 of FIG. 5B is the contact resistance between the fluid and the conductive element (contact resistance of fluid in inlet 172 contacting conductive element 178 and contact resistance of fluid in outlet 174 contacting conductive element 178). In FIG. 5C, small passage 176 enables the extra contact resistance to disappear.

Figure 5D:
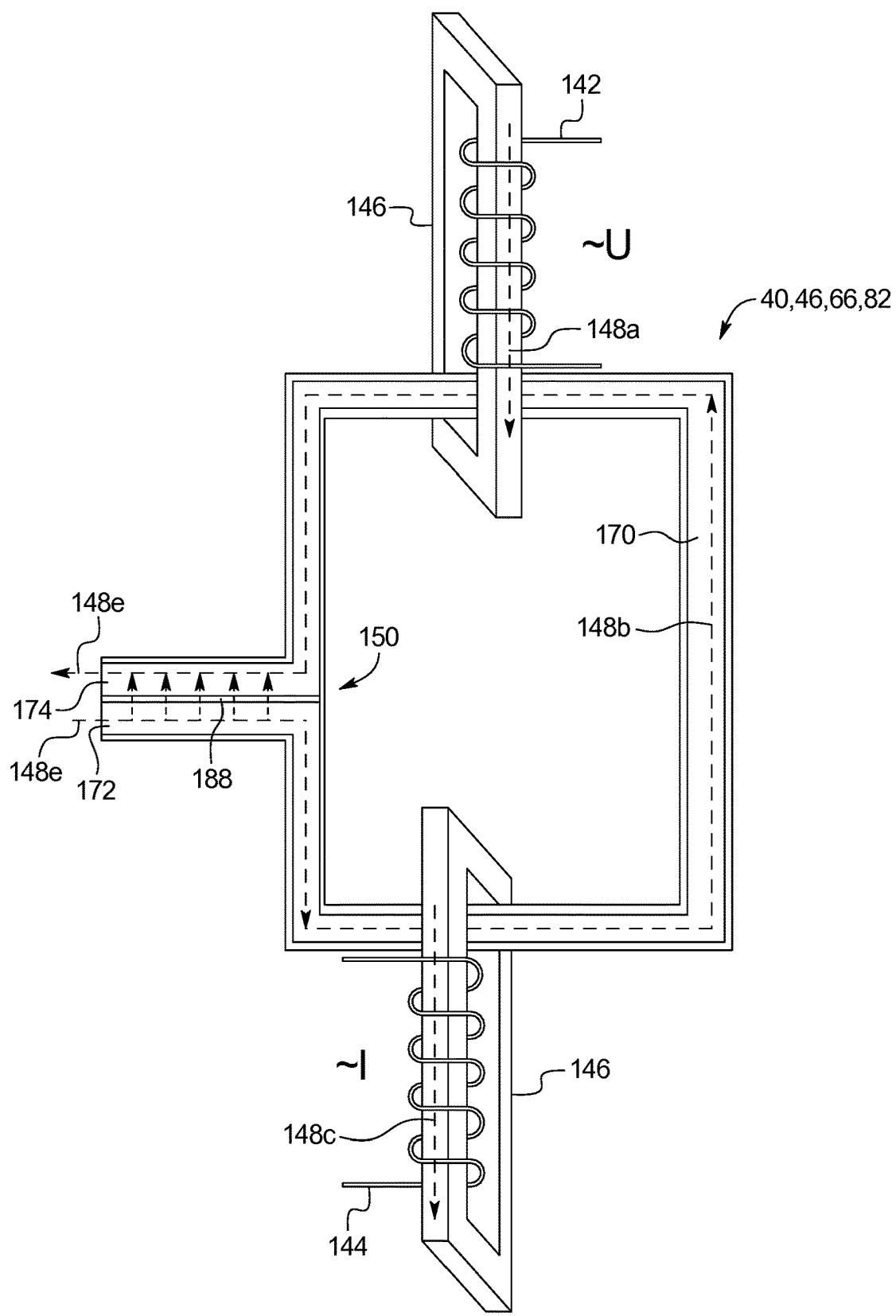
FIG. 5D is a schematic view yet another embodiment of an electrical bypass of the present disclosure.

FIG. 5D illustrates another alternative bypass 150 embodiment for the same type of conductivity sensor or cell 40, 46, 66, and 82, which includes first coil 142, second coil 144, each having an iron core 146 operating with a fluid flow path 170 having an inlet 172 and an outlet 174, wherein a desired current (arrow 148b) is promoted, while a stray current (arrow 148e) flowing through flow path 170 is minimized as much as possible. Here, instead of conductive element 178 (FIG. 5B) or small passage 176 (FIG. 5C), a conductive wall or partition 188 between the tubes of inlet 172 and outlet 174 is provided. Conductive wall or partition 188 may extend partially into or fully across the lumen (as illustrated) of flow path 170, so as to partially or fully occlude fluid flow, respectively, between inlet 172 and outlet 174. While FIG. 5D illustrates conductive wall or partition 188 entering flow path 170 and interrupting fluid flow, partition 188 may alternatively stop before entering flow path 170, allowing fluid to flow around the flow path.

Wall or partition 188 is in one embodiment made of a medically safe conductive plastic, such a medically safe plastic infused with conductive particles made of any of the materials listed above. Conductive wall or partition 188 in the illustrated embodiment is molded as a conductive part of flow path 170. Here again, two different plastics may be used, in which one part of the molded product has a conductive plastic (e.g., wall 188), while the other part of the molded product has a non-conductive plastic (e.g., outer wall of the inlet/outlet tube). Alternatively, the outer wall of the inlet/outlet tube is also conductive, creating a conductive tubing section that is sealed fluidically with non-conductive tubing that does not carry conductive wall or partition 188 or to a connector that does not carry conductive wall or partition 188. Conductive wall or partition 188 and associated tubing may be part of sensor 40, 46, 66, and 82 itself or be part of an add-on piece fluidically sealed between the sensor and the main flow path.

The large area of conductive contact between inlet 172 and outlet 174 and the small wall thickness provided by conductive wall or partition 188 ensures good electrical contact between the inlet and the outlet even if the material of wall or partition 188 is only a medium or good electrical conductor. Stray current (arrow 148e) should therefore be successfully discouraged from flowing through flow path 170. Also, the lesser conductivity of the conductive plastic and the relatively long distance needed to travel through flow path 170 should ensure that most of desired current (arrow 148b) will travel in flow path 170 and not out through conductive wall or partition 188. Some desired current (arrow 148b) will be lost in this way, but the operation of sensor 40, 46, 66, and 82 may be corrected accordingly via calibration.

It should be appreciated that while bypasses 150 of FIGS. 5B to 5D are illustrated with conductivity sensor or cell 40, 46, 66, and 82, they may be used alternatively with any type of sensor through which fluid flows in from an inlet and out through an outlet. Other such sensors may include temperature sensors, pressure sensors, ion sensors (e.g., sodium, calcium, potassium, etc.).

Figure 6:
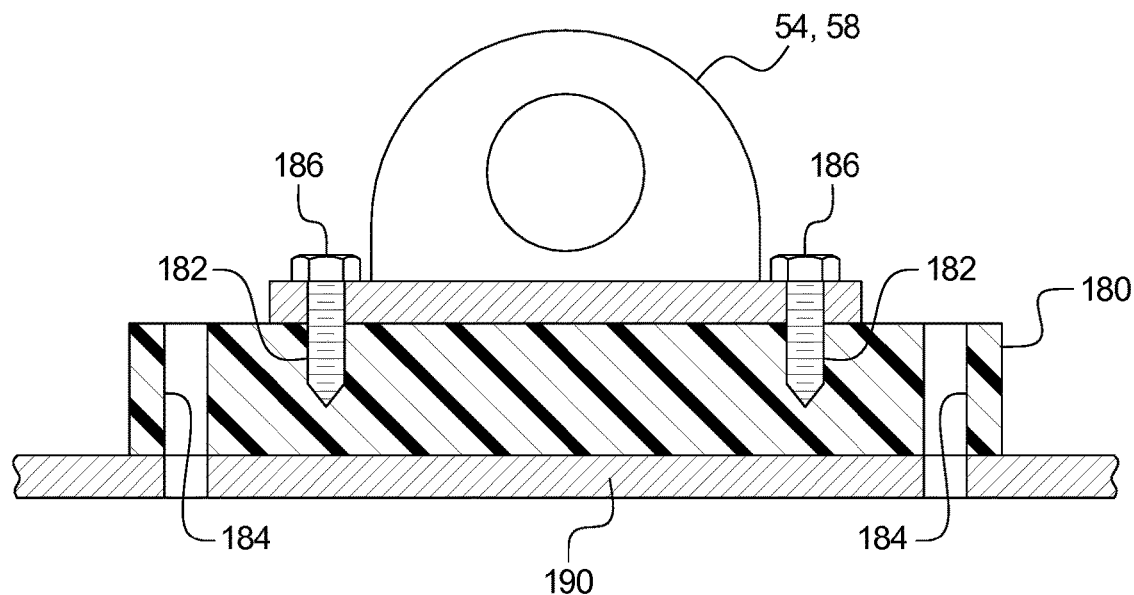
FIG. 6 is side elevation view of one embodiment for insulatingly mounting a flow component, so as to maintain the floating fluid pathway of the present disclosure.

Referring now to FIG. 6, to ensure that any fault voltage is dissipated through the floating fluid pathway, there may be no inadvertent paths to ground along the way. Inadvertent paths to ground are most likely to occur via flow components, such as pumps, having housings in conductive contact with the dialysis fluid or blood. Fault current may flow through conductive component housings, especially with pumps, such as peristaltic pumps, which occlude fluid flow and thereby increase electrical impedance in the fluid, forcing current into the pump housing.

In FIG. 6, a fluid flow component, such as fresh or spent dialysis fluid pump 54, 58, is mounted to an electrical insulator or insulating block 180, which may be plastic (e.g., polyethylene ("PE"), polypropylene ("PP")) or rubber (e.g., silicone)) for example. Plastic or rubber insulating block 180 includes threaded mounting holes 182 that are spaced apart to match the mounting hole footprint of, for example, fresh or used dialysis fluid pump 54, 58. Threaded mounting holes 182 may have metal threaded inserts that will not strip easily. Plastic or rubber insulating block 180 includes outer mounting holes 184 that are spaced apart to match a mounting hole footprint of machine chassis or frame 190, which may be made of a conductive metal, such as steel or aluminum. Plastic or rubber electrical insulator or insulating block 180 (i) separates metal screws 186 used to mount fresh or used dialysis fluid pump 54, 58 from machine chassis or frame 90 and (ii) metal screws or bolts (not illustrated) used to mount insulating block 180 to frame 90 from fresh or used dialysis fluid pump 54, 58. Any current due to a fault condition flowing through the housing of fresh or used dialysis fluid pump 54, 58 is therefore forced back into the fluid, e.g., into dialysis fluid of the floating fluid pathways described herein.

Figure 7A:
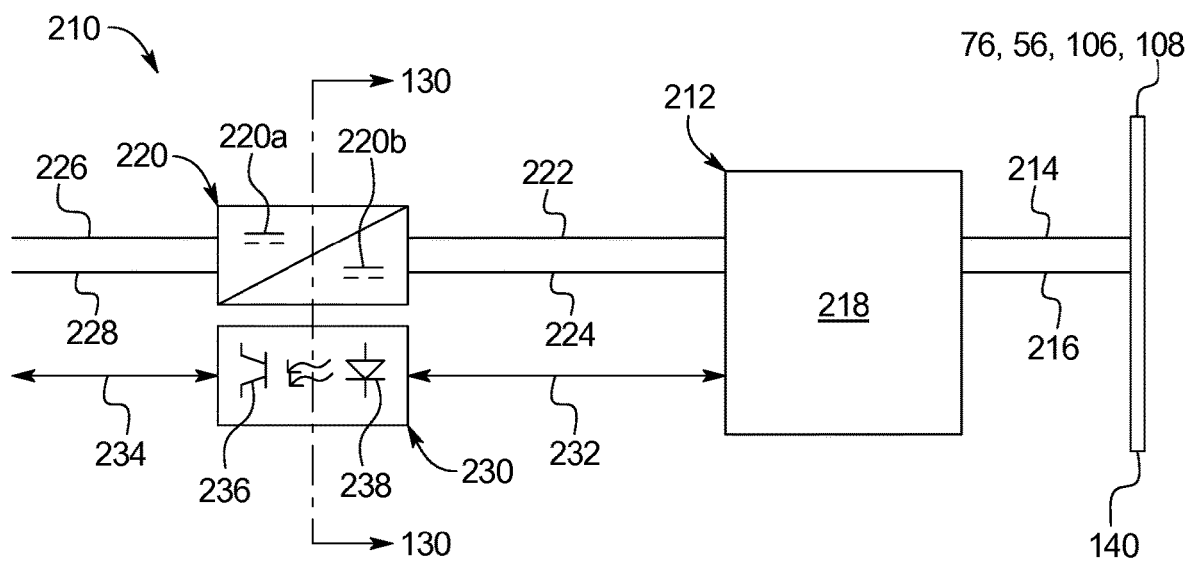
FIG. 7A is a schematic view of one embodiment for electrically isolating sensing component so as to maintain a floating fluid pathway of the present disclosure.

FIG. 6 illustrates an embodiment for electrically insulating a mechanical mounting of a component. Referring now to FIG. 7A, circuit 210 illustrates one embodiment electrically insulating or isolating an electrical coupling of an electrical component, such as a sensor 212 that contacts the dialysis fluid and/or blood pathways, e.g., a conductivity sensor or flow sensor. In the illustrated embodiment, sensor 212 is a conductivity sensor including electrodes 214 and 216 that contact a dialysis fluid or blood line, such as fresh dialysis fluid line 76, used dialysis fluid line 56, or blood lines 106, 108. Electrodes 214 and 216 extend from sensor electronics 218. Sensor electronics 218 receives local power, e.g., 5 VDC, via local power and ground lines 222 and 224 extending respectively from a DC to DC converter 220.

DC to DC converter 220 receives system DC power, e.g., 24 VDC, via system power and ground wires 226 and 228, respectively. DC to DC converter 220 may perform the isolated energy transfer in different ways, for example, it may employ opto-coupling as shown in isolated signal interface 230. Or, DC to DC converter 220 may switch first from DC to AC, wherein an AC input circuit uses a coil to magnetically couple to an output coil of an output AC circuit of output 220b, which is then converted to a desired output DC voltage, e.g., 5 VDC. The desired output voltage is applied to local power and ground lines 222 and 224 for powering sensor electronics 218. The physical gap between input coil 220a and output coil 220b of DC to DC converter 220 prevents fault or stray currents from traveling either direction (from input coil to output coil and from output coil to input coil) within DC to DC converter 220. It should be appreciated that DC to DC converter 220 may step DC voltages up (e.g., from 5 VDC to 24 VDC), step DC voltages down (e.g., from 24 VDC to 5 VDC), or keep the voltages the same (e.g., 5 VDC on both input and output coils or 24 VDC on both input and output coils).

Circuit 210 also includes an isolated signal interface 230, which conductively decouples the input/output signal of sensor electronics 218 sent along signal line 232 from the input/output signal of isolated signal interface 230 sent along signal line 234. The electrical isolation of isolated signal interface 230 may be provided in a number of ways known to those of skill in the art. In the illustrated embodiment, transistor 236 is optically isolated from a light-emitting diode 238, such that there is no actual physical connection between transistor 236 and diode 238 to transmit a fault current from machine 12 to the floating fluid pathway 140 or vice versa. It is also possible that a signal may be sent to an electronic device 218, in which case isolated signal interface 230 may place transistor 236 in the overall applied part 130 and light-emitting diode 238 in the non-applied part (to the left of line 130 in FIG. 7A). It is further possible that isolated signal interface 230 may provide two-way signaling, with one transistor 236/diode 238 pair provided as illustrated in FIG. 7A (for signals from electronic device 218), and another diode 238/transistor 236 pair switched as just described for signaling to electronic device 218.

The electrical decoupling provided by isolated signal interface 230, much like that of DC to DC converter 220 and of insulating block 180 in FIG. 6, prevents (i) fault or stray currents traveling in fluid pathways 76, 56, 106, 108, etc., from entering the system and potentially corrupting other system components, and (ii) fault or stray currents emanating from machine 12 along signal line 234 from entering fluid pathways 76, 56, 106, 108.

As indicated by the arrows and dash-dot line in FIG. 7A, structure to the right of the dash-dot line is included in overall applied part 130, while structure to the left of the dash-dot line is not. Thus, fluid pathways 76, 56, 106, 108, fluid contacting electrodes 214 and 216, power lines 222 and 224, output coil 220b, signal line 232 and light-emitting diode 238 become part of overall applied part 130, while input coil 220a, power and ground lines 226 and 228, transistor 236 and signal line 234 are electrically isolated from the overall applied part 130.

Figure 7B:
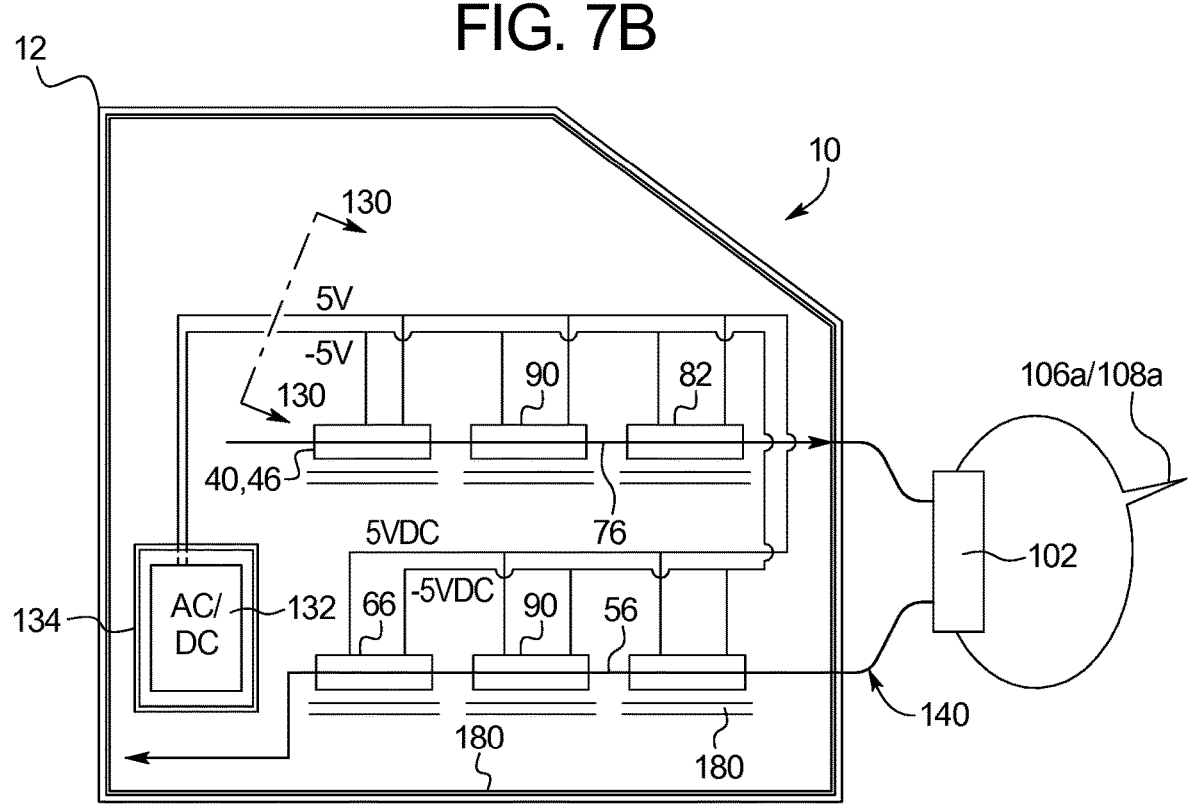
FIGS. 7B to 7D illustrate different implementations for the electrical isolation embodiment of FIG. 7A.
Figure 7C:
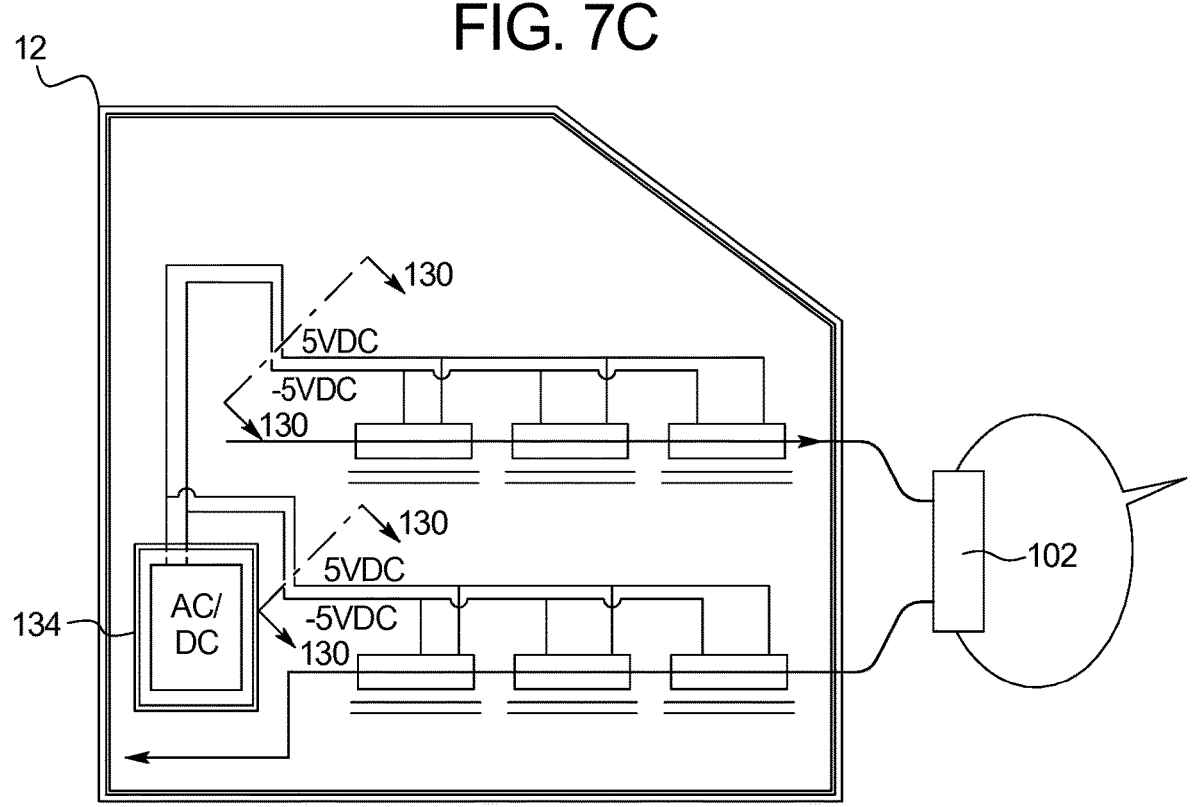
Figure 7D:
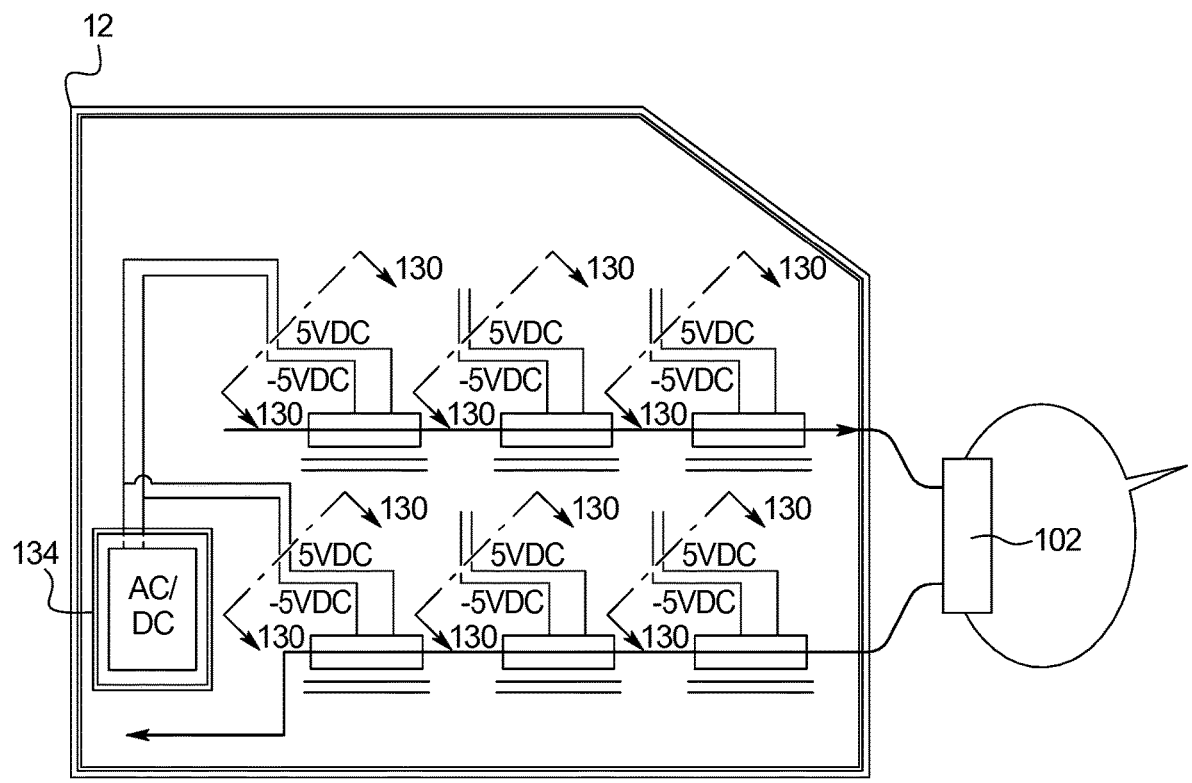

FIGS. 7B to 7D illustrate different ways in which electrical isolation using circuit 210 may be implemented. FIGS. 7B to 7D illustrate the power supply portion of circuit 210 (DC power lines 222, 224, 226 and 228 and DC to DC converter 220), however, the alternatives illustrated in FIGS. 7B to 7D apply equally to the signal portion of circuit 210 (not shown in FIGS. 7B to 7D). Power supply 132 as discussed in connection with FIG. 3A includes its own first layer of electrical insulation 134. The second layer of electrical insulation is indicated by the dash-dot line (described in FIG. 7A) separating the applied part 130 (generally to the right of the line) from the non-applied part 130 (generally to the left of the line).

FIG. 7B illustrates a single dash-dot line of separation for applied part 130 for the sensing equipment 40, 46, 90, 82, and 66, etc., of both fresh and used dialysis fluid lines 76 and 56. That is, a single output coil 220*b* may supply DC voltage to sensing equipment 40, 46, 90, 82, and 66 of both dialysis fluid lines 76 and 56. FIG. 7C illustrates a separate dash-dot line of separation for the applied part 130 for the sensing equipment 40, 46, 90, 82, and 66, etc., of fresh versus used dialysis fluid lines 76 and 56. That is, a first output coil 220*b* of a first DC to DC converter 220 may supply DC voltage to sensing equipment 40, 46, 90, 82, and 66 of fresh dialysis fluid line 76, while a second output coil 220*b* of a second DC to DC converter 220 may supply DC voltage to sensing equipment 40, 46, 90, 82, and 66 of used dialysis fluid line 56.

FIG. 7D illustrates a separate dash-dot line of separation for the applied part 130 for each piece of sensing equipment 40, 46, 90, 82, and 66, etc., of fresh and used dialysis fluid lines 76 and 56. That is, a separate output coil 220*b* of a separate DC to DC converter 220 is provided for each piece of sensing equipment 40, 46, 90, 82, and 66, etc., of dialysis fluid circuit 30. Alternatively, a separate dash-dot line of separation for applied part 130 may be provided for two or more but less than all sensing equipment 40, 46, 90, 82, and 66 of fresh dialysis fluid line 76 and two or more but less than all sensing equipment 40, 46, 90, 82, and 66 of used dialysis fluid line 56.

As discussed above, in FIGS. 6 and 7A to 7D, the dialysis fluid and the blood of floating fluid pathway 140 along with anything that is in conductive contact with the dialysis fluid and blood define an overall applied part 130 of system 10. The mechanical and electrical examples of FIGS. 6 and 7A to 7D, respectively, both provide system 10 with a well-defined electrically insulating border or boundary for the overall applied part 130.

As discussed above, in FIGS. 6 and 7A to 7D, the dialysis fluid and the blood of floating fluid pathway 140 along with anything that is in conductive contact with the dialysis fluid and blood in the machine 12 (including anything in contact with the fluids in the concentrate containers and concentrate lines, fresh dialysis fluid line 76, fresh dialysis fluid tube 78, used dialysis fluid tube 80, used dialysis fluid line 56, dialyzer 102, arterial line 106, venous line 108, and associated needles 106*a*/108*a*) define an overall applied part 130 of system 10. The mechanical and electrical examples of FIGS. 6 and 7A to 7D, respectively, each provide system 10 with a well-defined electrically insulating border or boundary for the overall applied part 130.

It should be understood that various changes and modifications to the presently preferred embodiments described herein will be apparent to those skilled in the art. Such changes and modifications may be made without departing from the spirit and scope of the present invention and without diminishing its intended advantages. It is therefore intended that such changes and modifications be covered by the appended claims.

The invention is claimed as follows:

1. A renal failure therapy system comprising:
   a dialyzer;
   a blood circuit in fluid communication with the dialyzer;
   a dialysis fluid circuit in fluid communication with the dialyzer; and
   an electrically floating fluid pathway comprising at least a portion of the blood circuit and at least a portion of the dialysis fluid circuit, wherein the only electrical path to ground is via used dialysis fluid traveling through the renal failure therapy system to earth ground,
   wherein at least one electrical component in the at least a portion of the dialysis fluid circuit of the electrically floating fluid pathway is electrically bypassed, and
   wherein the at least a portion of the dialysis fluid circuit includes at least a portion of a fresh dialysis fluid line and at least a portion of a used dialysis fluid line.

2. The renal failure therapy system of claim 1, wherein (i) the electrically bypassed portion of the dialysis fluid circuit of the electrically floating fluid pathway is electrically short circuited or (ii) the electrical component is of a type sensitive to electrical disturbances.

3. The renal failure therapy system of claim 1, wherein the electrically bypassed portion of the dialysis fluid circuit of the electrically floating fluid pathway includes (i) at least one electrical line placed in parallel with the at least one electrical component, (ii) a small passage formed between a fluid inlet and a fluid outlet to the at least one electrical component, or (iii) a conductor located between the fluid inlet and the fluid outlet of the at least one electrical component.

4. The renal failure therapy system of claim 3, wherein the at least one electrical line placed in parallel with the at least one electrical component includes upstream and downstream conductive couplers placed in fluid lines upstream and downstream, respectively, of the electrical component, and wherein the electrical line is extended from the upstream conductive coupler to the downstream conductive coupler.

5. The renal failure therapy system of claim 1, wherein the at least one electrical component includes a conductivity sensor having a conductivity probe that contacts dialysis fluid flowing through the at least a portion of the dialysis fluid circuit.

6. The renal failure therapy system of claim 1, wherein the at least one electrical component includes a flowmeter for measuring the flowrate of dialysis fluid flowing through the at least a portion of the dialysis fluid circuit.

7. The renal failure therapy system of claim 1, comprising at least one electrically bypassed electrical component in the at least a portion of the fresh dialysis fluid line and at least one electrically bypassed electrical component in the at least a portion of the used dialysis fluid line.

8. The renal failure therapy system of claim 1, wherein the electrically floating fluid pathway includes an electrical line extending from the at least a portion of the fresh dialysis fluid line to the at least a portion of the used dialysis fluid line, the electrical line positioned to bypass the dialyzer and a patient to be treated.

9. The renal failure therapy system of claim 1, wherein the electrically floating fluid pathway includes at least one selected from the group consisting of an arterial line, a venous line, arterial and venous needles, a fresh dialysis fluid line, a fresh dialysis fluid tube, liquid concentrate lines, concentrate sources if liquid concentrate sources are used, a water line, a water source if the water is non-deionized, a used dialysis fluid tube, and a used dialysis fluid line.

10. The renal failure therapy system of claim 1, wherein the electrically floating fluid pathway is connected to an external drain line, which leads to an electrically grounded drain.

11. The renal failure therapy system of claim 1, wherein the electrically floating fluid pathway includes at least one fluid component that is not electrically bypassed, but which is electrically insulated from a chassis of the system to form a delineated applied part.

12. A renal failure therapy system comprising:
a dialyzer;
a blood circuit in fluid communication with the dialyzer;
a dialysis fluid circuit in fluid communication with the dialyzer, the dialysis fluid circuit including a fresh dialysis fluid line and a used dialysis fluid line;
a first electrical component operable with the fresh dialysis fluid line;
a first electrical bypass shunting current away from the first electrical component;
a second electrical component operable with the used dialysis fluid line; and
a second electrical bypass shunting current away from the second electrical component.

13. The renal failure therapy system of claim 12, wherein the first and second electrical bypasses are part of an electrically floating fluid pathway in which the only electrical path to ground is via used dialysis fluid traveling through the renal failure therapy system to earth ground.

14. The renal failure therapy system of claim 13, wherein the electrically floating fluid pathway includes a plurality of fluid operating components located along the fresh dialysis fluid line and the used dialysis fluid line, wherein the fluid operating components are not electrically bypassed.

15. The renal failure therapy system of claim 14, wherein the plurality of fluid operating components include at least one selected from the group consisting of (i) a pump and (ii) a component mounted to a system chassis via an electrical insulator.

16. The renal failure therapy system of claim 12, wherein the first and second electrical bypasses contact fluid upstream and downstream of the first and second electrical components, respectively, the fluid electrically connecting the first and second electrical bypasses.

17. A renal failure therapy machine operating with a dialyzer and a blood circuit in fluid communication with the dialyzer, the machine comprising:
a dialysis fluid circuit in fluid communication with the dialyzer, the dialysis fluid circuit including a fresh dialysis fluid line and a used dialysis fluid line; and
an electrically floating fluid pathway, wherein the only electrical path to ground is via used dialysis fluid traveling through the renal failure therapy machine to earth ground, and including an electrical bypass from the fresh dialysis fluid line to the used dialysis fluid line, such that a fault current generated in the fresh dialysis fluid line bypasses the dialyzer via the electrical bypass to the used dialysis fluid line.

18. The renal failure therapy machine of claim 17, wherein the electrical bypass is (i) located between a furthest downstream fluid component of the fresh dialysis fluid line and the dialyzer, or (ii) located between a furthest upstream fluid component of the used dialysis fluid line and the dialyzer.

19. The renal failure therapy machine of claim 17, wherein the electrically floating fluid pathway includes at least one additional electrical bypass shunting current away from an electrical component located in the fresh or used dialysis fluid lines.

20. A renal failure therapy system comprising:
a dialyzer;
a blood circuit in fluid communication with the dialyzer;
a dialysis fluid circuit in fluid communication with the dialyzer;
an electrically floating fluid pathway comprising at least a portion of the dialysis fluid circuit, wherein the only electrical path to ground is via used dialysis fluid traveling through the renal failure therapy system to earth ground, and wherein at least one electrical component in the at a least portion of the dialysis fluid circuit of the electrically floating fluid pathway is electrically insulated; and
a testing structure configured to test whether the electrically floating fluid pathway has been compromised via an undesired electrical connection to ground, wherein the testing structure optionally includes a generator selected from the group consisting of a current generator and a voltage generator, and a meter selected from the group consisting of a voltage meter and a current meter,
wherein the system is programmed to use (i) the generator to set a limit and (ii) the meter to determine if the limit has been reached,
wherein the testing structure includes an electrical path from at least one bypass bypassing the at least one electrical component to ground, and
wherein the meter is in the electrical path.

21. The renal failure therapy system of claim 20, wherein the testing structure includes the generator and the meter, the system includes a switch in electrical communication with the generator, and the system is programmed to close the switch before treatment for (i) and open the switch during treatment for (ii).

22. The renal failure therapy system of claim 20, wherein the testing structure includes the meter placed in electrical communication with first and second bypasses shunting current away from the at least one electrical component located in fresh or used dialysis fluid lines.

23. A renal failure therapy system comprising:
a dialyzer;
a blood circuit in fluid communication with the dialyzer;
a dialysis fluid circuit in fluid communication with the dialyzer; and
an electrically floating fluid pathway comprising at least a portion of the blood circuit and at least a portion of the dialysis fluid circuit, wherein the only electrical path to ground is via used dialysis fluid traveling through the renal failure therapy system to earth ground, and wherein at least one electrical component in the at least a portion of the dialysis fluid circuit of the electrically floating fluid pathway includes an electrical bypass having (i) a small passage formed between a fluid inlet and a fluid outlet to the at least one electrical component, or (ii) a conductor located between the fluid inlet and the fluid outlet of the at least one electrical component.

24. A renal failure therapy system comprising:
a dialyzer;
a blood circuit in fluid communication with the dialyzer;
a dialysis fluid circuit in fluid communication with the dialyzer; and
an electrically floating fluid pathway comprising at least a portion of the blood circuit and at least a portion of the dialysis fluid circuit, wherein the only electrical path to ground is via used dialysis fluid traveling through the renal failure therapy system to earth ground,
wherein at least one electrical component in the at least a portion of the dialysis fluid circuit of the electrically floating fluid pathway is electrically bypassed, and
wherein the at least one electrical component includes a conductivity sensor having a conductivity probe that contacts dialysis fluid flowing through the at least a portion of the dialysis fluid circuit.

25. A renal failure therapy system comprising:
a dialyzer;
a blood circuit in fluid communication with the dialyzer;
a dialysis fluid circuit in fluid communication with the dialyzer; and
an electrically floating fluid pathway comprising at least a portion of the blood circuit and at least a portion of the dialysis fluid circuit, wherein the only electrical path to ground is via used dialysis fluid traveling through the renal failure therapy system to earth ground,
wherein at least one electrical component in the at least a portion of the dialysis fluid circuit of the electrically floating fluid pathway is electrically bypassed, and
wherein the electrically floating fluid pathway includes at least one selected from the group consisting of an arterial line, a venous line, arterial and venous needles, a fresh dialysis fluid line, a fresh dialysis fluid tube, liquid concentrate lines, concentrate sources if liquid concentrate sources are used, a water line, a water source if the water is non-deionized, a used dialysis fluid tube, and a used dialysis fluid line.

26. A renal failure therapy system comprising:
a dialyzer;
a blood circuit in fluid communication with the dialyzer;
a dialysis fluid circuit in fluid communication with the dialyzer; and
an electrically floating fluid pathway comprising at least a portion of the blood circuit and at least a portion of the dialysis fluid circuit, wherein the only electrical path to ground is via used dialysis fluid traveling through the renal failure therapy system to earth ground,
wherein at least one electrical component in the at least a portion of the dialysis fluid circuit of the electrically floating fluid pathway is electrically bypassed, and
wherein the electrically floating fluid pathway is connected to an external drain line, which leads to an electrically grounded drain.

* * * * *